US011959138B2

(12) United States Patent
George et al.

(10) Patent No.: US 11,959,138 B2
(45) Date of Patent: *Apr. 16, 2024

(54) METHODS AND COMPOSITIONS FOR NUCLEIC ACID SEQUENCING USING PHOTOSWITCHABLE LABELS

(71) Applicant: Illumina Cambridge Limited, Cambridge (GB)

(72) Inventors: Wayne N. George, Cambridge (GB); Andrew A. Brown, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/867,018

(22) Filed: Jul. 18, 2022

(65) Prior Publication Data

US 2023/0055284 A1 Feb. 23, 2023

Related U.S. Application Data

(63) Continuation of application No. 16/830,798, filed on Mar. 26, 2020, now Pat. No. 11,421,271.

(60) Provisional application No. 62/825,593, filed on Mar. 28, 2019.

(51) Int. Cl.
*C12Q 1/68* (2018.01)
*C12Q 1/6869* (2018.01)

(52) U.S. Cl.
CPC .................. *C12Q 1/6869* (2013.01)

(58) Field of Classification Search
CPC .................................... C12Q 1/6869
See application file for complete search history.

(56) References Cited

U.S. PATENT DOCUMENTS

| | | |
|---|---|---|
| 5,302,509 A | 4/1994 | Cheeseman et al. |
| 5,429,807 A | 7/1995 | Matson et al. |
| 5,436,327 A | 7/1995 | Southern et al. |
| 5,561,071 A | 10/1996 | Hollenberg et al. |
| 5,583,211 A | 12/1996 | Coassin et al. |
| 5,658,734 A | 8/1997 | Brock et al. |
| 5,837,858 A | 11/1998 | Brennan et al. |
| 5,874,219 A | 2/1999 | Rava et al. |
| 5,919,523 A | 7/1999 | Sundberg et al. |
| 6,136,269 A | 10/2000 | Winkler et al. |
| 6,172,218 B1 | 1/2001 | Brenner et al. |
| 6,287,768 B1 | 9/2001 | Chenchik et al. |
| 6,287,776 B1 | 9/2001 | Hefti et al. |
| 6,288,220 B1 | 9/2001 | Kambara et al. |
| 6,291,193 B1 | 9/2001 | Khodadoust et al. |
| 6,297,006 B1 | 10/2001 | Drmanac et al. |
| 6,346,413 B1 | 2/2002 | Fodor et al. |
| 6,355,431 B1 | 3/2002 | Chee et al. |
| 6,416,949 B1 | 7/2002 | Dower et al. |
| 6,465,178 B2 | 10/2002 | Chappa et al. |
| 6,482,591 B2 | 11/2002 | Lockhart et al. |
| 6,514,751 B2 | 2/2003 | Johann et al. |
| 6,524,793 B1 | 2/2003 | Chandler et al. |
| 6,610,482 B1 | 8/2003 | Fodor et al. |
| 11,421,271 B2 | 8/2022 | George et al. |
| 2002/0102578 A1 | 8/2002 | Dickinson et al. |
| 2010/0009353 A1 | 1/2010 | Barnes et al. |
| 2014/0079923 A1 | 3/2014 | George et al. |

FOREIGN PATENT DOCUMENTS

| | | |
|---|---|---|
| EP | 0 742 287 | 11/1996 |
| EP | 0 799 897 | 10/1997 |
| WO | WO 93/17126 | 9/1993 |
| WO | WO 95/11995 | 5/1995 |
| WO | WO 95/35505 | 12/1995 |
| WO | WO 98/44151 | 10/1998 |
| WO | WO 98/59066 | 12/1998 |
| WO | WO 00/06770 | 2/2000 |
| WO | WO 00/18957 | 4/2000 |
| WO | WO 00/31148 | 6/2000 |
| WO | WO 00/53812 | 9/2000 |
| WO | WO 00/63437 | 10/2000 |
| WO | WO 01/01143 | 1/2001 |
| WO | WO 01/57248 | 8/2001 |
| WO | WO 02/12566 | 2/2002 |
| WO | WO 03/014392 | 2/2003 |
| WO | WO 04/018493 | 3/2004 |
| WO | WO 04/018497 | 3/2004 |
| WO | WO 05/047301 | 5/2005 |
| WO | WO 05/065814 | 7/2005 |
| WO | WO 07/020457 | 2/2007 |
| WO | WO 07/107775 | 9/2007 |
| WO | WO 2013/044018 | 3/2013 |
| WO | WO 2014/139596 | 9/2014 |

OTHER PUBLICATIONS

Chozinski et al., 2014, Twinkle, twinkle little star: photoswitchable fluorophores for super-resolution imaging, FEBS Letters, 588:3603-3612.
Cusido et al., 2016, A photochromic bioconjugate with photoactivatable fluorescence for superresolution imaging, J. Phys. Chem., 120:12860-12870.
Drmanac et al., 2010, Human genome sequencing using unchained base reads on self-assembling DNA nanoarrays, Science 327(5961):78-81.
Guillier et al., 2000, Linkers and cleavage strategies in solid-phase organic synthesis and combinatorial chemistry, Chem. Rev. 100:2092-2157.
Heilemann et al., Feb. 24, 2009, Photoswitches: key molecules for subdiffraction-resolution fluorescence imaging and molecular quantification, Laser & Photonics Reviews, 3(1-2):180-202.
Li et al., Sep. 17, 2018, Switchable fluorophores for single-molecule localization microscopy, Chemical Reviews, 118(18):9412-9454.

(Continued)

*Primary Examiner* — Jezia Riley
(74) *Attorney, Agent, or Firm* — Knobbe, Martens, Olson & Bear, LLP

(57) ABSTRACT

Embodiments of the present disclosure relate to nucleotides labeled with photoswitchable compounds. Also provided herein are methods and kits of using these labeled nucleotides for sequencing applications.

21 Claims, 2 Drawing Sheets

(56) References Cited

OTHER PUBLICATIONS

Margulies, Sep. 15, 2005, Genome sequencing in microfabricated high-density picolitre reactors, Nature, 437:376-380.
Shendure et al., Sep. 9, 2005, Accurate multiplex polony sequencing of an evolved bacterial genome, Science, 309(5741):1728-1732.
Singer et al., 2010, Reversibly photoswitchable nucleosides: synthesis and photochromic properties of diarylethene-functionalized 7-deasaadenosine derivatives, J. Am. Chem. Soc, 132:8372-8377.
Song et al., Jul. 2002, A photochromic acceptor as a reversible light-driven switch in fluorescence resonance energy transfer, Journal of Photochemistry and Photobiology, A: Chemistry, 150(1-3):177-185.
Stratagene Catalog, 1988, Gene characterization kits, p. 39.
Uhlman et al., Jun. 1990, Antisense oligonucleotides: a new therapeutic principle, Chemical Reviews, 90(4):543-584.
Xiong et al., 2016, Photoswitchable spiropyran dyads for biological imaging, Org. Lett. 18:3666-3669.
International Search Report and Written Opinion dated Jun. 5, 2020 in application No. PCT/EP2020/058763.

METHODS AND COMPOSITIONS FOR NUCLEIC ACID SEQUENCING USING PHOTOSWITCHABLE LABELS

INCORPORATION BY REFERENCE TO ANY PRIORITY APPLICATIONS

The present application is a continuation of U.S. application Ser. No. 16/830,798, filed Mar. 26, 2020, which claims the benefit of priority to U.S. Provisional Appl. No. 62/825,593, filed Mar. 28, 2019, each of which is incorporated by reference in its entirety.

BACKGROUND

Field

The present disclosure generally relates to nucleotides labeled with photoswitchable labels and their use in polynucleotide sequencing methods and applications.

The detection of analytes such as nucleic acid sequences that are present in a biological sample has been used as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting analytes such as nucleic acid sequences in a biological sample is nucleic acid sequencing.

It has become clear that the need for high-throughput, smaller, less expensive DNA sequencing technologies will be beneficial for reaping the rewards of genome sequencing. Personalized healthcare is moving toward the forefront and will benefit from such technologies; the sequencing of an individual's genome to identify potential mutations and abnormalities will be crucial in identifying if a person has a particular disease, followed by subsequent therapies tailored to that individual. To accommodate such an aggressive endeavor, sequencing should move forward and become amenable to high throughput technologies not only for its high throughput capabilities, but also in terms of ease of use, time and cost efficiencies, and clinician access to instruments and reagents.

Photoswitchable fluorescent probes are important new developments in the super-resolution fluorescence microscopy techniques, where dyes that can be switched from a dark to emissive state are required in order to access improved spatial resolution. See Vaughan et al., *FEBS Letters* 588 (2014) 3603-3612. Photoswitchable fluorescent probes utilize photochromic compounds, which switch reversibly between states with distinct absorption spectra upon illumination by light of suitable wavelength and intensity. The photo generated species typically revert back to the starting species by either thermal means or further illumination. For example, Anderson et al. recently reported the synthesis of a small molecule dyad consisting of a red emitting fluorophore that is covalently linked to a photoswitchable quencher and the use of the dyad for biological imaging. See Anderson et al., *Org. Lett.* 2016, 18, 3666-3669. In similar work, Bossi et al. reported the synthesis of a dyad with a coumarin fluorophore and an oxazine photochrome that is conjugated with an antibody for super resolution imaging. See Bossi et al., *J. Phys. Chem. C* 2016, 120, 12860-12870.

There exists a need to develop new photoswitchable fluorescent labels that can be utilized in biological imaging applications, including next generation sequencing applications.

SUMMARY

Some embodiments of the present disclosure relate to a nucleotide conjugate comprising a photoswitchable label, the photoswitchable label comprises a fluorescent moiety covalently bonded, optionally via a linker, to a photochromic moiety. Upon irradiation with a light source such as a laser or a LED light, the photoswitchable label may undergo reversible change from an "on" state to an "off" state, or vice versa. In some embodiments, the fluorescent moiety of the nucleotide conjugate may be a red emitting fluorophore, for example, a silicon rhodamine. In some embodiments, the photochromic moiety of the photoswitchable label comprises a spiropyrano or spirothiopyrano moiety having a structure of formula (I):

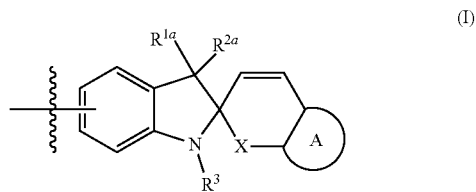

wherein X is O (oxygen) or S (sulfur);
each of $R^{1a}$ and $R^{2a}$ is independently selected from the group consisting of H, halo, optionally substituted $C_{1-6}$ alkyl, optionally substituted $C_{2-6}$ alkenyl, optionally substituted $C_{2-6}$ alkynyl, $C_{1-6}$ haloalkyl, $C_{1-6}$ alkoxy, and $C_{1-6}$ haloalkoxy;
$R^3$ is selected from the group consisting of H, $C_{1-6}$ alkyl, and $-(CH_2)_n-R^4$;
$R^4$ is selected from the group consisting of $C_{6-10}$ aryl, 5 to 10 membered heteroaryl, 3 to 7 membered carbocyclyl, and 3 to 7 membered heterocyclyl, each optionally substituted;
ring A is $C_{6-10}$ aryl or 5 to 10 membered heteroaryl, each substituted with at least one electron withdrawing group; and
n is an integer of 1 to 6.

In some other embodiments, the photochromic moiety of the photoswitchable label comprises a structure of formula (II):

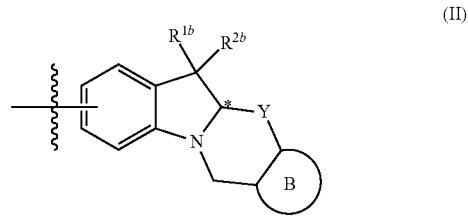

wherein Y is O (oxygen) or S (sulfur);
each of $R^{1b}$ and $R^{2b}$ is independently selected from the group consisting of H, halo, optionally substituted $C_{1-6}$ alkyl, optionally substituted $C_{2-6}$ alkenyl, optionally substituted $C_{2-6}$ alkynyl, $C_{1-6}$ haloalkyl, $C_{1-6}$ alkoxy, and $C_{1-6}$ haloalkoxy; and ring B is $C_{6-10}$ aryl or 5 to 10 membered heteroaryl; each substituted with at least one electron withdrawing group; and wherein * indicates the attachment point to the fluorescent moiety.

Some embodiments of the present disclosure relate to oligonucleotides or polynucleotides comprising a nucleotide conjugate described herein.

Some further embodiments of the present disclosure relate to methods for determining nucleotide sequences of target polynucleotides, comprising performing a sequencing reaction that comprises one or more cycles of:

(i) incorporating different types of nucleotide conjugates into a plurality of polynucleotides complementary to the target polynucleotides to produce extended polynucleotides, wherein each of a first type of nucleotide conjugates comprises a first photoswitchable label, each of a second type of nucleotide conjugates comprises a second photoswitchable label, and each of a third type of nucleotide conjugates comprises a third label;

(ii) detecting a first collection of signals from the extended polynucleotides in each cycle via a first imaging event;

(iii) irradiating the extended polynucleotides after the first imaging event with a light source to cause changes in emission signals of the first photoswitchable label and the second photoswitchable label;

(iv) detecting a second collection of signals from the extended polynucleotides via a second imaging event; and determining the sequences of the target polynucleotides based on the sequentially incorporated nucleotide conjugates. In some embodiments, four different types of nucleotide conjugates are simultaneously present and compete for incorporation into the polynucleotides complementary to the target polynucleotides during the incorporation in each cycle. In some such embodiments, the incorporation of the first type of the nucleotide conjugates is determined from a signal state in the first imaging event and a dark state in the second imaging event. In some such embodiments, the incorporation of the second type of the nucleotide conjugates is determined from a dark state in the first imaging event and a signal state in the second imaging event. In some such embodiments, the incorporation of the third type of the nucleotide conjugates is determined from a signal state in the first imaging event and second imaging event. In some such embodiments, the incorporation of the fourth type of the nucleotide conjugates is determined from a dark state in the first imaging event and second imaging event. In some further embodiments, the first type of nucleotide conjugate comprises a photochromic moiety of formula (I) and the second type of nucleotide conjugate comprises a photochromic moiety of formula (II).

Some further embodiments of the present disclosure relate to kits comprising one or more types of nucleotide conjugates with photoswitchable labels, as set forth herein. The kits may be used to in applications such as sequencing, expression analysis, hybridization analysis, genetic analysis, RNA analysis, cellular assay (e.g., cell binding or cell function analysis), or protein assay (e.g., protein binding assay or protein activity assay). The use may be on an automated instrument for carrying out a particular technique, such as an automated sequencing instrument. The sequencing instrument may contain only one laser to distinguish between different detectable labels. The sequencing instrument may contain additional laser or light source operating at a different wavelength for activating the photoswitchable labels from an "on" state to an "off" state, or vice versa.

DETAILED DESCRIPTION

Figures 1A, 1B:
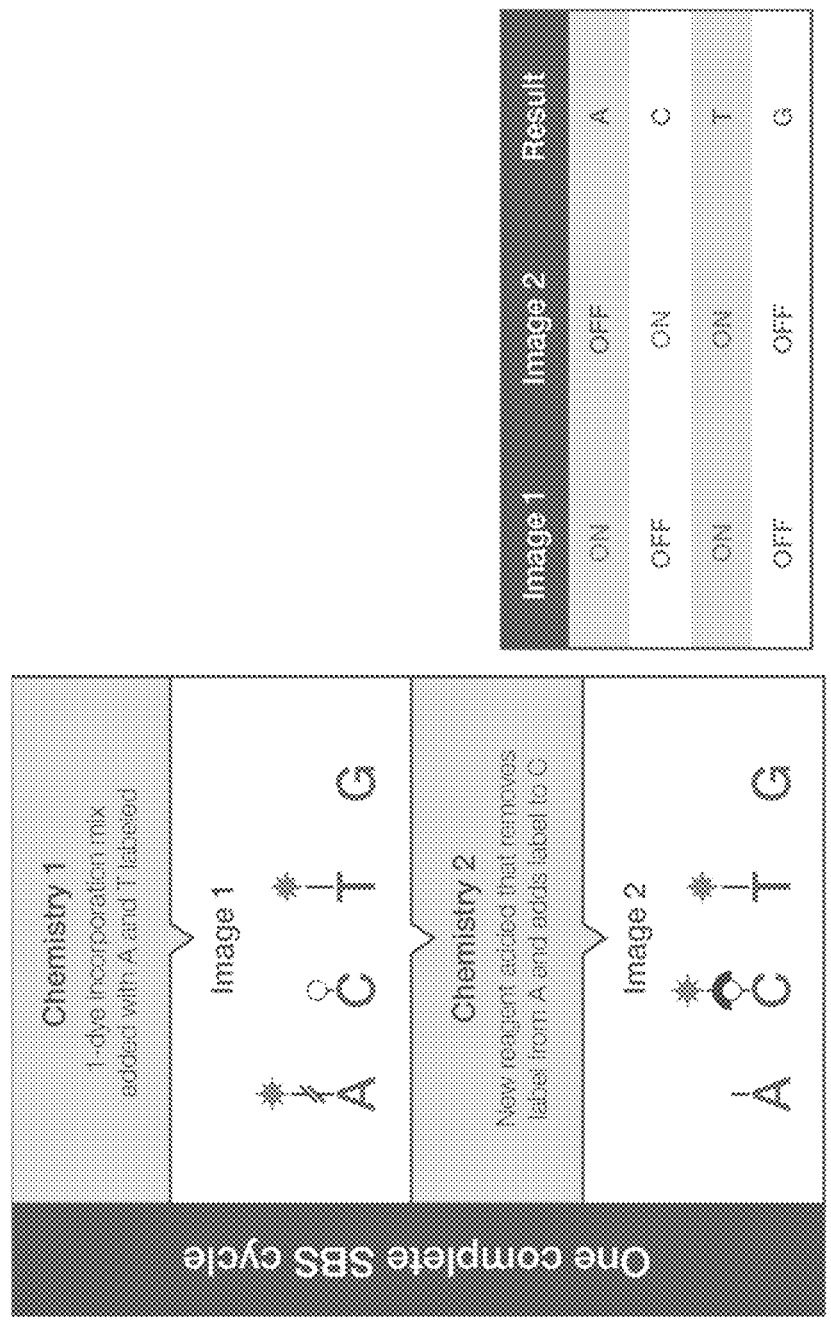
FIG. 1A illustrates a flowchart for the standard Illumina one-channel sequencing-by-synthesis (SBS) chemistry.
FIG. 1B illustrates how Image 1 and Image 2 from standard one-channel SBS are processed by image analysis software to identify which bases are incorporated.

Illumina's Next-Generation Sequencing system, the iSeq 100™ uses a CMOS-based technology to deliver a simplified, accessible benchtop sequencing solution. The standard sequencing workflow is illustrated in FIGS. 1A and 1B, which is also referred to as the 1-channel sequencing. Each sequencing cycle includes two chemistry steps and two imaging steps. In FIG. 1A, the first chemistry step exposes the flow cell to a mixture of nucleotides that have fluorescently labeled adenines and thymines. During the first imaging step, the light emission from each cluster is recorded by the CMOS sensor. The second chemistry step removes the fluorescent label from adenine and adds a fluorescent label to cytosine. In both chemistry steps, guanine is dark (unlabeled). The second image is recorded. In FIG. 1B, the combination of Image 1 and Image 2 are processed by image analysis software to identify which bases are incorporated at each cluster position. This sequencing cycle is repeated "n" times to create a read length of "n" bases. Unlike four-channel SBS chemistry, where sequencers use a different dye for each nucleotide, the iSeq 100™ System uses one dye per sequencing cycle. In one-channel chemistry, adenine has a removable label and is labeled in the first image only. Cytosine has a linker group that can bind a label and is labeled in the second image only. Thymine has a permanent fluorescent label and is therefore labeled in both images, and guanine is permanently dark. Nucleotides are identified by analysis of the different emission patterns for each base across the two images.

Embodiments of the present disclosure relate to a new method for determining nucleotide sequences of target polynucleotides. In particular, the method involves the use of nucleotides labeled with photoswitchable dyes, which are capable of undergoing photo induced color change upon irradiation with a light source.

There are several advantages associated with the use of photoswitchable fluorophores. The photoswitchable dyes do not need to display switching robustness as they are only required for a single imaging event and are cleaved immediately thereafter. It is known that these dyes can be switched multiple times without any display of fatigue resistance. This approach also eliminates the use of introducing a dedicated cleave mix or exchange reagent as the conversion of the emissive state of the dye is induced "remotely" via photonic energy. The total cycle time should also be minimized as the switching occurs on a sub-microsecond timescale substantially reducing the time required to pump reagents into and out of the flowcell. Conversion based on irradiation is typically high yielding, an essential characteristic to avoid mixed signals or suppressed emission.

In addition, the ability to exert control over the emissive states of fluorescent markers is very useful in nucleic acid sequencing applications. For example, a commonly observed problem with many similar tags is that after they have been successfully used in a process step, residual emission can contribute to unwanted background signal. Remotely inducing a change in the emission profile, based on isomerization, conformational changes or reversible ring-opening processes offers the possibility to improve signal to noise ratio.

In some embodiments, the method may include the following steps:
(a) performing a sequencing reaction that comprises repeated cycles of:
(i) incorporating four different types of nucleotide conjugates into a plurality of polynucleotides complementary to the target polynucleotides to produce extended polynucleotides, wherein each of a first type of nucleotide conjugates comprises a first photoswitchable label, each of a second type of nucleotide conjugates comprises a second photoswitchable label, and each of a third type of nucleotide conjugates comprises a third label;
(ii) detecting a first collection of signals from the extended polynucleotides in each cycle via a first imaging event;
(iii) irradiating the extended polynucleotides after the first imaging event with a light source to cause changes in emission signals of the first photoswitchable label and the second photoswitchable label;
(iv) detecting a second collection of signals from the extended polynucleotides via a second imaging event;
(b) determining the sequences of the target polynucleotides based on the sequentially incorporated nucleotide conjugates.

In some embodiments, the incorporation of the first type of the nucleotide conjugates is determined from a signal state in the first imaging event and a dark state in the second imaging event; the incorporation of the second type of the nucleotide conjugates is determined from a dark state in the first imaging event and a signal state in the second imaging event; the incorporation of the third type of the nucleotide conjugates is determined from a signal state in the first imaging event and second imaging event; and the incorporation of a fourth type of the nucleotide conjugates is determined from a dark state in the first imaging event and second imaging event.

A "signal state," when used in reference to a detection event, means a condition in which a specific signal is produced in the detection event. For example, a nucleotide subunit can be in a signal state and detectable when attached to a fluorescent label that is detected in a fluorescence detection step by excitation and emission of that fluorescent label in a sequencing method. The term "dark state," when used in reference to a detection event, means a condition in which a specific signal is not produced in the detection event. For example, a nucleotide subunit can be in a dark state when the nucleotide lacks a fluorescent label and/or does not emit fluorescence that is specifically detected in a fluorescent detection step of a sequencing method. Dark state detection may also include any background fluorescence which may be present absent a fluorescent label. For example, some reaction components may demonstrate minimal fluorescence when excited at certain wavelengths. As such, even though there is not a fluorescent moiety present there may be background fluorescence from such components. Further, background fluorescence may be due to light scatter, for example from adjacent sequencing reactions, which may be detected by a detector. As such, "dark state" can include such background fluorescence as when a fluorescent moiety is not specifically included, such as when a nucleotide lacking a fluorescent label is utilized in methods described herein. However, such background fluorescence is contemplated to be differentiatable from a signal state and as such nucleotide incorporation of an unlabeled nucleotide (or "dark" nucleotide) is still discernible.

In some embodiments of the method described herein, step (a) is repeated at least 50 times, 100 times, 150 times, 200 times, 250 times, 300 times, 350 times, 400 times, 450 times, or 500 times. In some embodiments, the four different types of nucleotide conjugates are simultaneously present and compete for incorporation during each cycle. In some further embodiments, the incorporation of the nucleotide conjugates is performed by a polymerase.

In some embodiments, different types of nucleotide conjugates comprise reversible terminator moieties. In some further embodiments, step (a) further includes cleaving the reversible terminator moieties from incorporated nucleotide conjugates prior to the next incorporation cycle. In some further embodiments, the nucleotide conjugates comprise nucleotide types selected from the group consisting of dATP, dTTP, dUTP, dCTP, dGTP, and non-natural nucleotide analogs thereof.

In some embodiments of the method described herein, the labels of the first type of nucleotide conjugates and the third type of nucleotide conjugates may comprise the same fluorescent moieties. In another embodiment, the labels of the second type of nucleotide conjugates and the third type of nucleotide conjugates may comprise the same fluorescent moieties. In other embodiments, the labels of the first type of nucleotide conjugates, the second type of nucleotide conjugates, and the third type of nucleotide conjugates may comprise different fluorescent moieties. The different fluorescent moieties may be detected either using the same emission filter, or different emission filters. In some embodiments, the fourth type of nucleotide conjugates is not labeled with a fluorescent moiety. In some embodiments of the method described herein, the irradiating in step (a)(iii) does not change or substantially change the signal detected from the third label of the third type of nucleotide conjugates In some embodiments, the irradiating light source in step (a)(iii) may comprise a laser, a light-emitting diode (LED), or a combination thereof. In some embodiments, the irradiating light source in step (a)(iii) has a different wavelength than the excitation wavelength used in the first imaging event. In some such embodiments, the irradiating light source in step (a)(iii) may have a wavelength of about 350 nm to about 450 nm. In one embodiment, the irradiating light source in step (a)(iii) has a wavelength of about 405 nm.

In some embodiments of the method described herein, the first imaging event and the second imaging event have the same or substantially the same excitation wavelength. In such embodiments, the first label, the second label and the third label can be detected using one detection channel. In some such embodiments, the first imaging event and the second imaging event may have an excitation wavelength of about 550 nm to about 650 nm. In one embodiment, the first imaging event and the second imaging event have an excitation wavelength of about 633 nm.

First Photoswitchable Label

In some embodiments of the method described herein, upon irradiation with a light source described herein step (a)(iii), the emission signal of the first photoswitchable label changes, for example, from a signal state to a dark state. In other word, the emission signal observed may be switched from "on" to "off."

In some embodiments, the first photoswitchable label comprises a first fluorescent moiety covalently bonded, optionally via a first linker, to a first photochromic moiety. In some embodiments, the first linker may be part of the pi-conjugation system of the first fluorescent moiety. In some such embodiments, the first fluorescent moiety comprises a fluorophore emitting a red light, for example, a red light with a wavelength between about 600 nm to about 700 nm. In some such embodiments, the first fluorescent moiety comprises a silicon rhodamine fluorophore. In one embodiment, the rhodamine fluorophore comprises the structure:

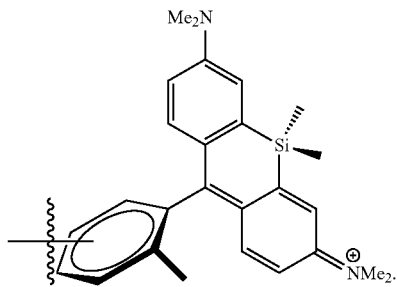

In some embodiments, the first photochromic moiety may comprise a spiropyrano or spirothiopyrano moiety. In some such embodiment, the first photochromic moiety comprises the structure of formula (I):

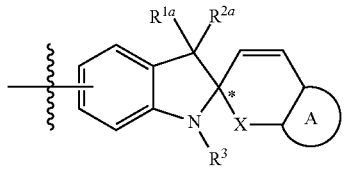

wherein X is O (oxygen) or S (sulfur);

each of $R^{1a}$ and $R^{2a}$ is independently selected from the group consisting of H, halo, optionally substituted $C_{1-6}$ alkyl, optionally substituted $C_{2-6}$ alkenyl, optionally substituted $C_{2-6}$ alkynyl, $C_{1-6}$ haloalkyl, $C_{1-6}$ alkoxy, and $C_{1-6}$ haloalkoxy;

$R^3$ is selected from the group consisting of H, $C_{1-6}$ alkyl, and —$(CH_2)_n$—$R^4$;

$R^4$ is selected from the group consisting of $C_{6-10}$ aryl, 5 to 10 membered heteroaryl, 3 to 7 membered carbocyclyl, and 3 to 7 membered heterocyclyl, each optionally substituted;

ring A is $C_{6-10}$ aryl or 5 to 10 membered heteroaryl, each substituted with at least one electron withdrawing group; and n is an integer of 1 to 6.

In some such embodiments, the irradiating step (a)(iii) causes a break of the spiro carbon*-X bond in formula (I), resulting in a ring opening reaction that converts the first photochromic moiety into a quencher that is capable suppressing the emission of the first fluorescent moiety. In some instances, the break of the spiro carbon*-X bond is reversible.

In some embodiments of the first photochromic moiety of formula (I), the phenyl moiety fused to the five-membered pyrrolidine may be optionally substituted. In some embodiments, X is S. In some further embodiments, each $R^{1a}$ and $R^{2a}$ is $C_{1-6}$ alkyl, for example, each $R^{1a}$ and $R^{2a}$ is methyl. In some embodiments, ring A is phenyl or naphthyl substituted with at least one electron withdrawing group. Non-limiting examples of electron withdrawing groups may be selected from the group consisting of nitro, cyano, fluoro, bromo, —S(O)$_2$OH, triflyl (—S(O)$_2$CF$_3$), —OS(O)$_2$CF$_3$, ammonium, alkyl ammonium, $C_{1-6}$ alkyl substituted with one or more fluoro or bromo, and sulfonyl substituted with one or more fluoro or bromo.

In one embodiment, the first photochromic moiety comprises the structure of formula (Ia):

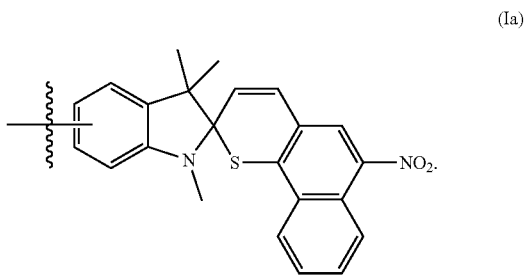

In one embodiment, the first photoswitchable label comprise the structure:

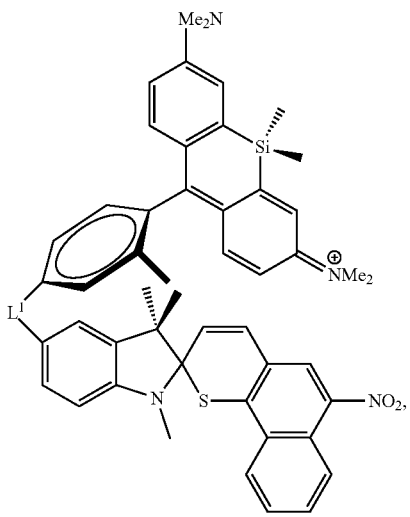

wherein $L^1$ is the first linker. In some such embodiment, the first linker $L^1$ may comprises an azido moiety. In some further embodiments, the first photoswitchable label is covalently attached to a nucleotide via the first linker, or via a different position either attached to the first photochromic moiety or the first fluorescent moiety.

Alternatively, the first photoswitchable label may comprises only a photochromic moiety and optionally a linker, where the photochromic moiety may act as a fluorophore by itself, capable of switching from a signal state to a dark state upon irradiation with a light source described in step (a)(iii).

Second Photoswitchable Label

In some embodiments of the method described herein, upon irradiation with a light source described in step (a)(iii), the emission signal of the second photoswitchable label changes, for example, from a non-emission dark state to a signal state. In other word, the emission signal observed may be switched from "off" to "on."

In some embodiments, the second photoswitchable label comprises a second fluorescent moiety covalently bonded to a second photochromic moiety, optionally via a second linker. In some embodiments, the second linker may be part of the pi-conjugation system of the second fluorescent moiety. In some embodiments, the second fluorescent moiety comprises a fluorophore emitting a red light, for example, a red light with a wavelength between about 600 nm to about 700 nm. In some such embodiments, In some such embodiments, the second fluorescent moiety comprises a coumarin fluorophore. In one embodiment, the coumarin fluorophore comprises the structure:

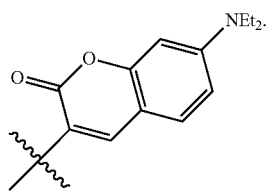

In some embodiments, the second photochromic moiety may comprise an oxazine moiety or a thiazine moiety. In some such embodiments, the second photochromic moiety comprises the structure of formula (II):

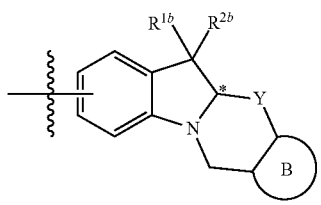

(II)

wherein Y is O (oxygen) or S (sulfur);
each of $R^{1b}$ and $R^{2b}$ is independently selected from the group consisting of H, halo, optionally substituted $C_{1-6}$ alkyl, optionally substituted $C_{2-6}$ alkenyl, optionally substituted $C_{2-6}$ alkynyl, $C_{1-6}$ haloalkyl, $C_{1-6}$ alkoxy, and $C_{1-6}$ haloalkoxy;
ring B is $C_{6-10}$ aryl or 5 to 10 membered heteroaryl; each substituted with at least one electron withdrawing group; and wherein * indicates the attachment point to the fluorescent moiety.

In some such embodiments, the irradiating step (a)(iii) causes a break of the carbon*-Y bond in formula (II), resulting in a ring opening reaction that activates the second fluorescent moiety to an emission state. In some instances, the break of the carbon*-Y bond is reversible.

In some embodiments of the second photochromic moiety of formula (II), the phenyl moiety fused to the five-membered pyrrolidine moiety may be optionally substituted. In some embodiments, Y is O. In some further embodiments, each $R^{1b}$ and $R^{2b}$ is $C_{1-6}$ alkyl, for example, each $R^{1b}$ and $R^{2b}$ is methyl. In some embodiments, ring B is phenyl or naphthyl substituted with at least one electron withdrawing group. In other embodiments, ring B may be selected from a six-membered heteroaryl, such as pyridyl or pyrimidyl. Non-limiting examples of electron withdrawing groups may be selected from the group consisting of nitro, cyano, fluoro, bromo, —S(O)$_2$OH, triflyl (—S(O)$_2$CF$_3$), —OS(O)$_2$CF$_3$, ammonium, alkyl ammonium, $C_{1-6}$ alkyl substituted with one or more fluoro or bromo, and sulfonyl substituted with one or more fluoro or bromo.

In one embodiment, the second photochromic moiety comprises the structure of formula (IIa):

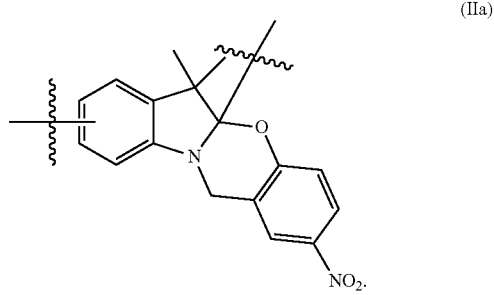

(IIa)

In one embodiment, the second photoswitchable label comprise the structure:

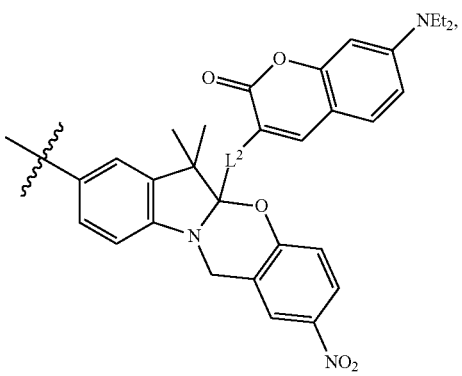

wherein $L^2$ is the second linker. In some such embodiment, the second linker $L^2$ may comprises pi-conjugated structure (for example, one or more double bonds). In one example, $L^2$ is a double bond connecting the coumarin and the second photochromic moiety. In some embodiments, the second photoswitchable label is covalently attached to the nucleotide either via the second linker, or via the point indicated by the squiggle line ~~~.

Alternatively, the second photoswitchable label may comprises only a photochromic moiety and optionally a linker, where the photochromic moiety may act as a fluorophore by itself, capable of switching from a non-emission dark state to an emission state upon irradiation with a light source described in step (a)(iii).

Non-limiting example of photoswitchable label or photochromic moieties may be used in the present application also include diarylethenes (e.g., bisthienylethene derivatives illustrated below), azines (e.g., azobenzenes illustrated below), photochromic quinones (e.g., phnoxynaphthacene quinone), spirooxazine, spirothiazines, mesoaldehyde 1-allyl-1-phenyl-2-phenylosazone, tetrachloro-1,2-ketonaphthalenone, thioindigoides, dinitrobenzylpyridine, and chromenes, etc.

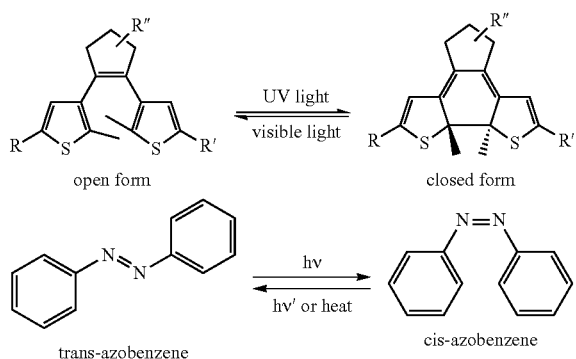

open form / closed form / trans-azobenzene / cis-azobenzene

In any embodiments of the method described herein, the plurality of extended polynucleotides are attached to a substrate, for example, a surface of a flowcell. In further embodiments, the polynucleotides are attached to the nanowells on the surface of the flowcell.

In any embodiments of the method described herein, detecting the first collection of signals and the second collection of signals comprises obtaining images of the substrate.

Additional illustrative embodiments are described below.

In some embodiments, methods for sequencing a nucleic acid comprise the use of one fluorescent labels for direct or indirect detection of three different nucleotide types and one nucleotide type that is not detected by the presence of a fluorescent signal but is instead detected by a lack or absence of a fluorescent signal. In some embodiments, methods for sequencing a nucleic acid comprise the use of two or more different fluorescent labels that comprise the same or similar excitation/emission spectra for direct or indirect detection of three different nucleotide types and one nucleotide type that is not detected by the presence of a fluorescent signal but is instead detected by a lack or absence of fluorescent signal. The same or similar excitation and emission spectra are such that a laser excites the two or more different fluorescent labels and an optical filter captures their emitted fluorescence signals. Detection of fluorescence to determine the sequence of a nucleic acid sample is performed in time space, for example at different times during a sequencing reaction (i.e., pre and post a change in reaction conditions such as enzymatic cleavage, change in environmental pH, addition of additional reagents), providing patterns of fluorescence such as fluorescence transitions patterns, their cumulative patterns determining the sequence of the nucleic acid target. As such, the methods described herein are time and cost efficient and allow for simplification of associated sequencing instrumentation.

An exemplary application of utilizing time space fluorescence pattern differences for determining a target nucleic acid sequence is sequence by synthesis (SBS) methodologies and technologies. As such, embodiments as described herein find particular utility in sequence by synthesis fluorescent applications. Even though embodiments as described herein are exemplary of innovative methods of fluorescent sequencing, the disclosed embodiments also find utility for a variety of other applications where detection of more than one analyte (i.e., nucleotide, protein, or fragments thereof) in a sample is desired.

In developing embodiments for sequencing using a minimal dye set, experimentation revealed alternative strategies for distinguishing between nucleotide incorporations using only one or two fluorescent moieties. These strategies provide for all four nucleotide types to be simultaneously present in a sequence cycle, and for the use of minimal dyes and optical filter sets. In some embodiments, no more than three fluorescent labels are utilized to determine the incorporation of all four nucleotide types that are present during a reaction, using one or two excitation and emission filters. In preferred embodiments no more than two fluorescent labels (or two or three of same or similar excitation/emission spectra) are utilized to determine the incorporation of all four nucleotide types that are all present during a reaction, using one excitation range of light and one detection emission filter.

In some embodiments, sequencing using a minimal dye set is performed on a substrate, such as a glass, plastic, semiconductor chip or composite derived substrate. In some embodiments, one nucleic acid species is provided on a substrate for example for single target sequencing. In other embodiments, sequencing can also be in a multiplex format, wherein multiple nucleic acid targets are detected and sequenced in parallel, for example in a flow cell or array type of format. Embodiments described herein are particularly advantageous when practicing parallel sequencing or massive parallel sequencing. Platforms practicing fluorescent parallel sequencing include, but are not limited to, those offered by Illumina, Inc. (e.g., HiSeq, Genome Analyzer, MiSeq, iSeq, iScan platforms), Life Technologies (e.g., SOLiD), Helicos Biosciences (e.g., Heliscope), 454/Roche Life Sciences (Branford, Conn.) and Pacific Biosciences (e.g., SMART). Flowcells, chips, and other types of surfaces that may accommodate multiple nucleic acid species are exemplary of substrates utilized for parallel sequencing. In multiplex formats wherein multiple nucleic acid species are sequenced in parallel, clonally amplified target sequences (e.g., via emulsion PCR (emPCR) or bridge amplification) are typically covalently immobilized on a substrate. For example, when practicing emulsion PCR the target of interest is immobilized on a bead, whereas clonally amplified targets are immobilized in channels of a flowcell or specific locations on an array or chip.

Flowcells for use with compositions and methods as described herein can be used in sequencing in a number of ways. For example, a DNA sample such as a DNA library can be applied to a flowcell or fluidic device comprising one or more etched flow channels, wherein the flowcell can further comprise a population of probe molecules covalently attached to its surface. The probes attached in the flowcell channels are advantageously located at different addressable locations in the channel and DNA library molecules can be added to the flowcell channels wherein complementary sequences can bind (as described herein, further as described in WO2012/096703, which is incorporated herein by reference in its entirety). Another example of a flowcell for use in the present application comprises a CMOS flowcell as described in U.S. Pat. Nos. 8,906,320 and 9,990,381 which is incorporated herein by reference in its entirety. Bridge amplification can be performed as described herein followed by sequencing by synthesis methods and compositions as described herein. Methods for creating and utilizing flowcells for sequencing are known in the art; references to which are provided herein and all of which are incorporated herein by reference in their entireties. It is contemplated that the methods and compositions as described herein are not limited to any particular manufacture or method of flowcell directed sequencing methodologies.

Sequencing utilizing the methods and compositions described herein can also be performed in a microtiter plate, for example in high density reaction plates or slides (Margulies et al., 2005, Nature 437(7057): 376-380, incorporated herein by reference in its entirety). For example, genomic targets can be prepared by emPCR technologies. Reaction plates or slides can be created from fiber optic material capable of capturing and recording light generated from a reaction, for example from a fluorescent or luminescent reaction. The core material can be etched to provide discrete reaction wells capable of holding at least one emPCR reaction bead. Such slides/plates can contain over a 1.6 million wells. The created slides/plates can be loaded with the target sequencing reaction emPCR beads and mounted to an instrument where the sequencing reagents are provided and sequencing occurs.

An example of arrayed substrates for sequencing targets utilizing compositions and methods as disclosed herein is provided when practicing patterned substrates comprising DNA nanoballs on a chip or slide as performed by Complete Genomics (Mountain View, Calif.). As described in Drmanac et al., 2010, Science 327(5961): 78-81, a silicon wafer can be layered with silicon dioxide and titanium and subsequently patterned using photolithography and dry etching techniques. The wafer can be treated with HMDS and coated with a photoresist layer to define discrete regions for silanization and subsequent covalent attachment of DNA nanoballs for sequencing. A skilled artisan will appreciate that many methods exist for creating slides/chips with discrete locations for immobilization of nucleic acids for use in sequencing methodologies and the present methods are not limited by the method in which a substrate is prepared for sequencing.

For purposes of illustration and not intended to limit embodiments as described herein, a general strategy sequencing cycle can be described by a sequence of steps. The following example is based on a sequence by synthesis sequencing reaction, however the methods as described herein as not limited to any particular sequencing reaction methodology.

The four nucleotide types A, C, T and G, typically modified nucleotides designed for sequencing reactions such as reversibly blocked (rb) nucleotides (e.g., rbA, rbT, rbC, rbG) wherein three of the four types are fluorescently labelled, are simultaneously added, along with other reaction components, to a location where the template sequence of interest is located and the sequencing reaction occurs (e.g., flowcell, chip, slide, etc.). Following incorporation of a nucleotide into a growing sequence nucleic acid chain based on the target sequence, the reaction is exposed to light and fluorescence is observed and recorded; this constitutes a first imaging event and a first fluorescence detection pattern. Following the first imaging event, the sample is irradiated with a light source to cause an identifiable and measurable changes in emission signals of the first and the second fluorescent labels. The reaction location is once again illuminated and any change in fluorescence is captured and recorded; constituting a second imaging event (i.e., a second fluorescence detection pattern). Blockers present on the incorporated nucleotides are removed and washed away along with other reagents present after the second imaging event in preparation for the next sequencing cycle. In some embodiments, the method of the present disclosure does not involve the use of any chemical reagents that may directly or indirectly cause an identifiable and measurable change in fluorescence from the first imaging event to the second imaging event. The fluorescence patterns from the two imaging events are compared and nucleotide incorporation, and thus the sequence of the target nucleic acid, for that particular cycle is determined.

Definitions

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
ddNTP Dideoxynucleotide triphosphate
ffN Fully functionalized nucleotide
LED Light emitting diode As used herein, the term "array" refers to a population of different probe molecules that are attached to one or more substrates such that the different probe molecules can be differentiated from each other according to relative location. An array can include different probe molecules that are each located at a different addressable location on a substrate. Alternatively, or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, any "R" group(s) represent substituents that can be attached to the indicated atom. An R group may be substituted or unsubstituted. If two "R" groups are described as "together with the atoms to which they are attached" forming a ring or ring system, it means that the collective unit of the atoms, intervening bonds and the two R groups are the recited ring. For example, when the following substructure is present:

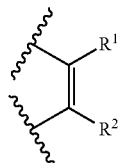

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

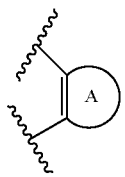

where A is an aryl ring or a carbocyclyl containing the depicted double bond.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_{1-4}$alkyl" or similar designations. By way of example only, "$C_{1-6}$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. The alkenyl group may be designated as "$C_{2-6}$alkenyl" or similar designations. By way of example only, "$C_{2-6}$alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. The alkynyl group may be designated as "$C_{2-6}$alkynyl" or similar designations. By way of example only, "$C_{2-6}$alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-6}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-6}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-carboxy" group refers to a "—C(=O)OR" group in which R is selected from the group consisting of hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes carboxyl (i.e., —C(=O)OH).

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

A "C-amido" group refers to a "—C(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, —CN, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfonyl, —$SO_3H$, —$OSO_2C_{1-4}$alkyl, and oxo (=O). Wherever a group is described as "optionally substituted" that group can be substituted with the above substituents.

The term "azido" as used herein refers to a —$N_3$ group.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

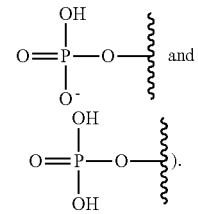

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Sometimes, "protecting group" and "blocking group" can be used interchangeably.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively, or additionally, the part of the spectrum can be one that passes through an interstitial region of a surface such as a region made of glass, plastic, silica, or other material set forth herein. In particular embodiments, radiation can be used that is capable of passing through a metal. Alternatively, or additionally, radiation can be used that is masked by glass, plastic, silica, or other material set forth herein.

Labeled Nucleotides

According to an aspect of the disclosure, the described nucleotide for incorporation comprises a detectable label and such nucleotide is called a labeled nucleotide. The label (e.g., a fluorescent dye) can be conjugated via an optional linker by a variety of means including hydrophobic attraction, ionic attraction, and covalent attachment. In some aspects, the dyes are conjugated to the substrate by covalent attachment. More particularly, the covalent attachment is by means of a linker group. In some instances, such labeled nucleotides are also referred to as "modified nucleotides." In some embodiments, the dye is covalently attached to the nucleotide via a cleavable linker. In some such embodiments, the cleavable linker may comprises one or more moieties including azido moiety, azidomethyl moiety, disulfide moiety, —(CH₂CH₂O)—, or any other covalent linker described herein.

Labeled nucleotides are useful for labeling polynucleotides formed by enzymatic synthesis, such as, by way of non-limiting example, in PCR amplification, isothermal amplification, solid phase amplification, polynucleotide sequencing (e.g., solid phase sequencing), nick translation reactions and the like.

In some embodiments, the dye may be covalently attached to oligonucleotides or nucleotides via the nucleotide base. For example, the labeled nucleotide or oligonucleotide may have the label attached to the C5 position of a pyrimidine base or the C7 position of a 7-deaza purine base through a linker moiety.

Unless indicated otherwise, the reference to nucleotides is also intended to be applicable to nucleosides. The present application will also be further described with reference to DNA, although the description will also be applicable to RNA, PNA, and other nucleic acids, unless otherwise indicated.

Some embodiments of the present disclosure relate to a nucleotide conjugate comprising a photoswitchable label, wherein photoswitchable label comprises a fluorescent moiety covalently bonded, optionally via a linker, to a photochromic moiety. In some embodiments, the photoswitchable label is attached to a nucleobase through a cleavable linker. In some further embodiments, the photoswitchable label is attached to the C5 position of a pyrimidine base or the C7 position of a 7-deaza purine base. In some embodiment, the nucleotide is labeled with a photoswitchable label. Upon irradiation with a light source, the emission signal of the photoswitchable label changes, for example, from a signal state to a dark state. In other word, the emission signal observed may be switched from "on" to "off." Alternatively, the photoswitchable label may change a non-emission dark state to a signal state. In other word, the emission signal observed may be switched from "off" to "on."

In some embodiments, the photoswitchable label comprises a fluorescent moiety covalently bonded, optionally via a linker, to a photochromic moiety. In some such embodiments, the fluorescent moiety comprises a fluorophore emitting a red light, for example, a red light with a wavelength between about 600 nm to about 700 nm.

In some embodiments, the fluorescent moiety of the photoswitchable label comprises a silicon rhodamine fluorophore. In one embodiment, the rhodamine fluorophore comprises the structure:

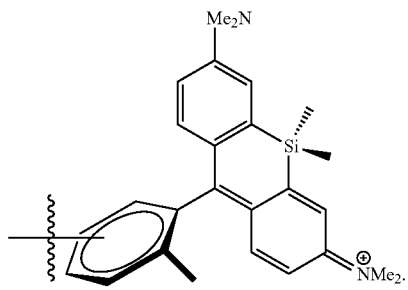

In some such embodiments, the photochromic moiety of the photoswitchable label may comprise a spiropyrano or spirothiopyrano moiety. For example, the photochromic moiety comprises the structure of formula (I):

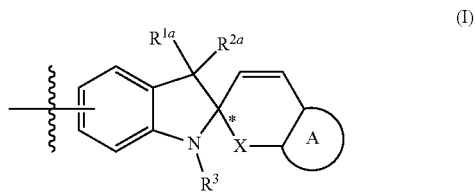

(I)

wherein the definition of X, $R^{1a}$, $R^{2a}$, $R^3$, $R^4$, and ring A are described herein, and wherein the carbon labeled with an asterisk * is the spiro carbon that will undergo chemical transformation upon irradiation with an appropriate light source.

In some embodiments of the photochromic moiety of formula (I), the phenyl moiety fused to the five-membered pyrrolidine may be optionally substituted. In some embodiments, X is S. In some further embodiments, each $R^{1a}$ and $R^{2a}$ is $C_{1-6}$ alkyl, for example, each $R^{1a}$ and $R^{2a}$ is methyl. In some embodiments, ring A is phenyl or naphthyl substituted with at least one electron withdrawing group. Non-limiting examples of electron withdrawing groups may be selected from the group consisting of nitro, cyano, fluoro, bromo, —S(O)₂OH, triflyl (—S(O)₂CF₃), —OS(O)₂CF₃, ammonium, alkyl ammonium, $C_{1-6}$ alkyl substituted with one or more fluoro or bromo, and sulfonyl substituted with one or more fluoro or bromo. In one embodiment, the photochromic moiety comprises the structure of formula (Ia):

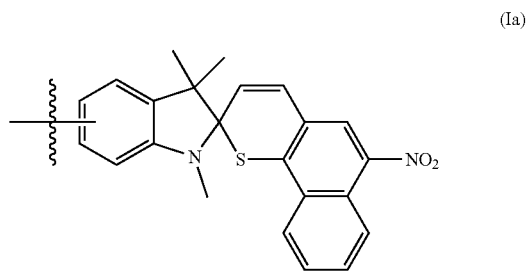

(Ia)

In one embodiment, the photoswitchable label comprise the structure:

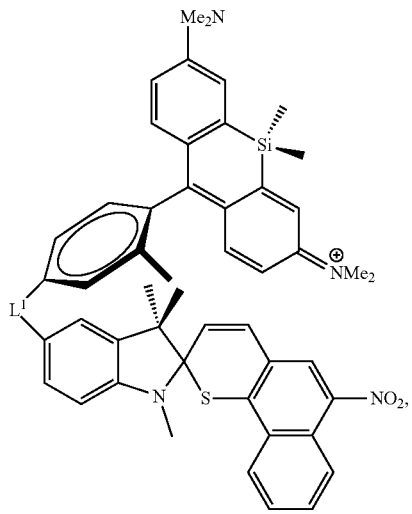

wherein L¹ is the first linker. In some such embodiment, the first linker L¹ may comprises an azido moiety. In some further embodiments, the first photoswitchable label is covalently attached to a nucleotide via the first linker, or via a different position either attached to the first photochromic moiety or the first fluorescent moiety.

In some other embodiments, the fluorescent moiety of the photoswitchable comprises a coumarin fluorophore. In one embodiment, the coumarin fluorophore comprises the structure:

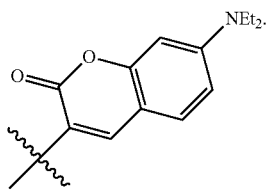

In some such embodiments, the photochromic moiety of the photoswitchable label may comprise an oxazine or thiazine moiety. For example, photochromic moiety comprises the structure of formula (II):

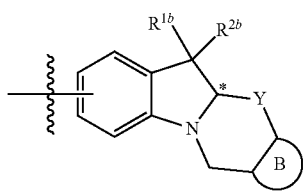

(II)

wherein the definition of Y, $R^{1b}$, $R^{2b}$, and ring B are described herein, and wherein carbon labeled with an asterisk * indicates the attachment point to the fluorescent moiety, either directly or via a second linker. The carbon*-Y bond in formula (II) will undergo a chemical transformation upon irradiation with an appropriate light source.

In some embodiments of the photochromic moiety of formula (II), the phenyl moiety fused to the five-membered pyrrolidine moiety may be optionally substituted. In some embodiments, Y is O. In some further embodiments, each $R^{1b}$ and $R^{2b}$ is $C_{1-6}$ alkyl, for example, each $R^{1b}$ and $R^{2b}$ is methyl. In some embodiments, ring B is phenyl or naphthyl substituted with at least one electron withdrawing group. In other embodiments, ring B may be selected from a six-membered heteroaryl, such as pyridyl or pyrimidyl. Non-limiting examples of electron withdrawing groups may be selected from the group consisting of nitro, cyano, fluoro, bromo, —S(O)₂OH, triflyl (—S(O)₂CF₃), —OS(O)₂CF₃, ammonium, alkyl ammonium, $C_{1-6}$ alkyl substituted with one or more fluoro or bromo, and sulfonyl substituted with one or more fluoro or bromo. In one embodiment, the photochromic moiety comprises the structure of formula (IIa):

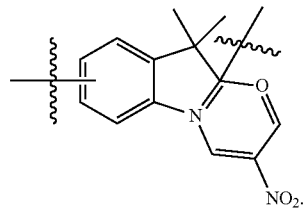

(IIa)

In one embodiment, the photoswitchable label comprise the structure:

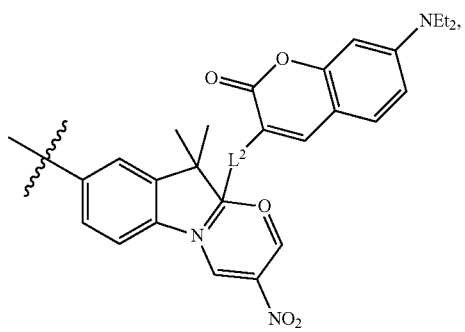

wherein L² is the second linker. In some such embodiment, the second linker L² may comprises pi-conjugated structure (for example, one or more double bonds). In one example, L² is a double bond connecting the coumarin and the photochromic moiety. In some embodiments, the photoswitchable label is covalently attached to the nucleotide either via the second linker L², or via the point indicated by the squiggle line ⁓.

Alternatively, the photoswitchable label described herein may comprises only a photochromic moiety and optionally a linker, where the photochromic moiety may act as a fluorophore by itself, capable of switching from a non-emission dark state to an emission state, or from an emission state to a dark state, upon irradiation with an appropriate light source.

Some further embodiments of the present disclosure relate to an oligonucleotide or polynucleotide comprising the nucleotide conjugate described herein.

Linkers

In some embodiments described herein, the purine or pyrimidine base of the nucleotide molecules can be linked to a detectable label as described above. In some such embodiments, the linkers used are cleavable. The use of a cleavable linker ensures that the label can, if required, be removed after detection, avoiding any interfering signal with any labeled nucleotide incorporated subsequently.

In some other embodiments, the linkers used are non-cleavable. Since in each instance where a labeled nucleotide described herein is incorporated, no nucleotides need to be subsequently incorporated and thus the label need not be removed from the nucleotide.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidizing agents, light, temperature, enzymes etc. The linker as discussed herein may also be cleaved with the same catalyst used to cleave the 3'-O-blocking group bond. Suitable linkers can be adapted from standard chemical protecting groups, as disclosed in Greene & Wuts, Protective Groups in Organic Synthesis, John Wiley & Sons. Further suitable cleavable linkers used in solid-phase synthesis are disclosed in Guillier et al. (*Chem. Rev.* 100:2092-2157, 2000).

Where the detectable label is attached to the base, the linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytosine, thymidine or uracil and the N-4 position on cytosine.

In some embodiments, the linker can comprise a spacer unit. The length of the linker is unimportant provided that the label is held a sufficient distance from the nucleotide so as not to interfere with any interaction between the nucleotide and an enzyme, for example, a polymerase.

In some embodiments, the linker may consist of the similar functionality as the 3'-OH protecting group. This will make the deprotection and deprotecting process more efficient, as only a single treatment will be required to remove both the label and the protecting group.

Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Useful linker groups may be found in PCT Publication No. WO2004/018493 (herein incorporated by reference), examples of which include linkers that may be cleaved using water-soluble phosphines or water-soluble transition metal catalysts formed from a transition metal and at least partially water-soluble ligands, for example, a Pd(II) complex and THP. In aqueous solution the latter form at least partially water-soluble transition metal complexes. Such cleavable linkers can be used to connect bases of nucleotides to labels such as the dyes set forth herein.

Particular linkers include those disclosed in PCT Publication No. WO2004/018493 (herein incorporated by reference) such as those that include moieties of the formulae:

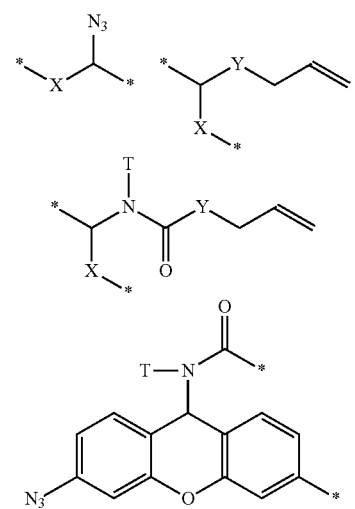

(wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_1$-$C_{10}$ substituted or unsubstituted alkyl group and * indicates where the moiety is connected to the remainder of the nucleotide). In some aspects, the linkers connect the bases of nucleotides to labels such as, for example, the dye compounds described herein.

Additional examples of linkers include those disclosed in U.S. Publication No. 2016/0040225 (herein incorporated by reference), such as those include moieties of the formulae:

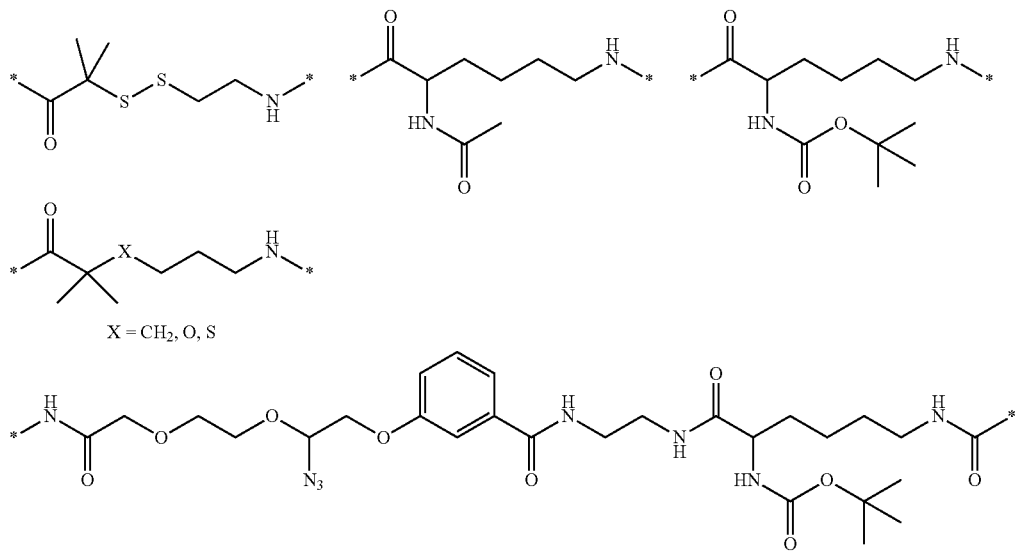

$X = CH_2, O, S$ (wherein * indicates where the moiety is connected to the remainder of the nucleotide). The linker moieties illustrated herein may comprise the whole or partial linker structure between the nucleotides/nucleosides and the labels.

In particular embodiments, the length of the linker between a fluorescent dye (fluorophore) and a guanine base can be altered, for example, by introducing a polyethylene glycol spacer group, thereby increasing the fluorescence intensity compared to the same fluorophore attached to the guanine base through other linkages known in the art. Exemplary linkers and their properties are set forth in PCT Publication No. WO2007020457 (herein incorporated by reference). The design of linkers, and especially their increased length, can allow improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula —$((CH_2)_2O)_n$—, wherein n is an integer between 2 and 50, as described in WO 2007/020457.

Nucleosides and nucleotides may be labeled at sites on the sugar or nucleobase. As known in the art, a "nucleotide" consists of a nitrogenous base, a sugar, and one or more phosphate groups. In RNA, the sugar is ribose and in DNA is a deoxyribose, i.e., a sugar lacking a hydroxy group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxy group attached to the C-3 or C-5 of the sugar. Nucleotides are usually mono-, di- or triphosphates.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. In particular embodiments, the derivatives should be capable of undergoing Watson-Crick pairing. "Derivative" and "analogue" also include, for example, a synthetic nucleotide or nucleoside derivative having modified base moieties and/or modified sugar moieties. Such derivatives and analogues are discussed in, for example, Scheit, *Nucleotide analogs* (John Wiley & Son, 1980) and Uhlman et al., *Chemical Reviews* 90:543-584, 1990. Nucleotide analogues can also comprise modified phosphodiester linkages including phosphorothioate, phosphorodithioate, alkyl-phosphonate, phosphoranilidate, phosphoramidate linkages and the like.

A dye may be attached to any position on the nucleotide base, for example, through a linker. In particular embodiments, Watson-Crick base pairing can still be carried out for the resulting analog. Particular nucleobase labeling sites include the C5 position of a pyrimidine base or the C7 position of a 7-deaza purine base. As described above a linker group may be used to covalently attach a dye to the nucleotide.

In particular embodiments the labeled nucleotide may be enzymatically incorporable and enzymatically extendable. Accordingly, a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labeled with the dyes described herein may have the formula:

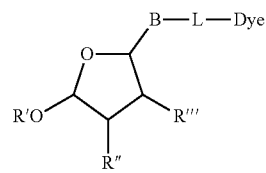

where Dye is a dye compound; B is a nucleobase, such as, for example uracil, thymine, cytosine, adenine, guanine and the like; L is an optional linker group which may or may not be present; R' can be H, monophosphate, diphosphate, triphosphate, thiophosphate, a phosphate ester analog, —O— attached to a reactive phosphorous containing group, or —O— protected by a blocking group; R" can be H, OH, a phosphoramidite, or a 3'-OH blocking group, and R'" is H or OH. Where R" is phosphoramidite, R' is an acid-cleavable hydroxyl protecting group which allows subsequent monomer coupling under automated synthesis conditions.

In a particular embodiment, the blocking group is separate and independent of the dye compound, i.e., not attached to it. Alternatively, the dye may comprise all or part of the 3'-OH blocking group. Thus R" can be a 3'-OH blocking group which may or may not comprise the dye compound.

In yet another alternative embodiment, there is no blocking group on the 3' carbon of the pentose sugar and the dye (or dye and linker construct) attached to the base, for example, can be of a size or structure sufficient to act as a block to the incorporation of a further nucleotide. Thus, the block can be due to steric hindrance or can be due to a combination of size, charge and structure, whether or not the dye is attached to the 3' position of the sugar.

In still yet another alternative embodiment, the blocking group is present on the 2' or 4' carbon of the pentose sugar and can be of a size or structure sufficient to act as a block to the incorporation of a further nucleotide.

The use of a blocking group allows polymerization to be controlled, such as by stopping extension when a nucleotide is incorporated. If the blocking effect is reversible, for example, by way of non-limiting example by changing chemical conditions or by removal of a chemical block, extension can be stopped at certain points and then allowed to continue.

In another particular embodiment, a 3'-OH blocking group will comprise a moiety disclosed in WO2004/018497 and WO2014/139596, which are hereby incorporated by references. For example the blocking group may be azidomethyl (—CH$_2$N3) or substituted azidomethyl (e.g., —CH(CHF$_2$)N$_3$ or CH(CH$_2$F)N$_3$), or allyl.

In a particular embodiment, the linker (between dye and nucleotide) and blocking group are both present and are separate moieties. In particular embodiments, the linker and blocking group are both cleavable under substantially similar conditions. Thus, deprotection and deblocking processes may be more efficient because only a single treatment will be required to remove both the dye compound and the blocking group. However, in some embodiments a linker and blocking group need not be cleavable under similar conditions, instead being individually cleavable under distinct conditions.

The disclosure also encompasses polynucleotides incorporating dye compounds. Such polynucleotides may be DNA or RNA comprised respectively of deoxyribonucleotides or ribonucleotides joined in phosphodiester linkage. Polynucleotides may comprise naturally occurring nucleotides, non-naturally occurring (or modified) nucleotides other than the labeled nucleotides described herein or any combination thereof, in combination with at least one nucleotide (e.g., labeled with a dye compound) as set forth herein. Polynucleotides according to the disclosure may also include non-natural backbone linkages and/or non-nucleotide chemical modifications. Chimeric structures comprised of mixtures of ribonucleotides and deoxyribonucleotides comprising at least one labeled nucleotide are also contemplated.

Non-limiting exemplary labeled nucleotides as described herein include:

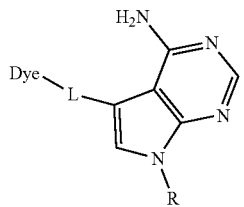
A

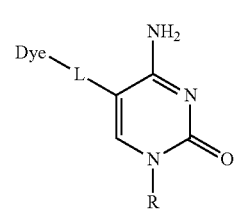
C

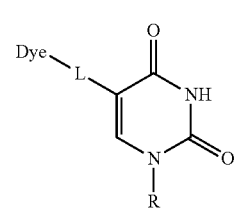
T

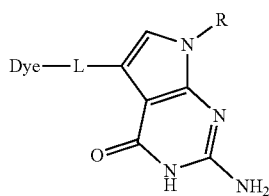
G

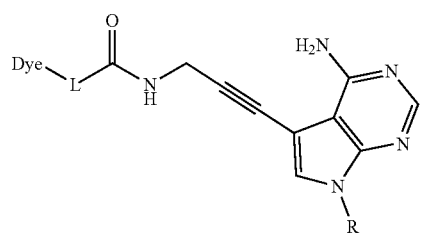
A

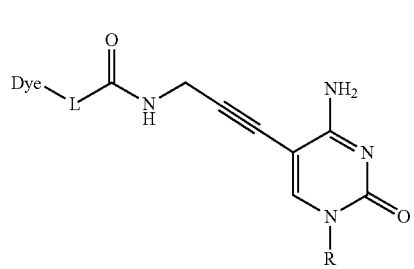
C

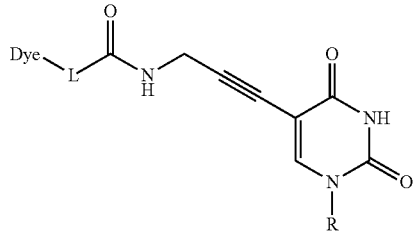
T

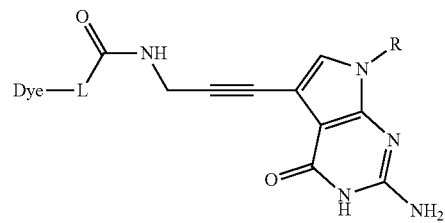
G wherein L represents a linker and R represents a sugar residue as described above, or with the 5' position substituted with one, two or three phosphates.

In some embodiments, non-limiting exemplary fluorescent dye conjugates are shown below:

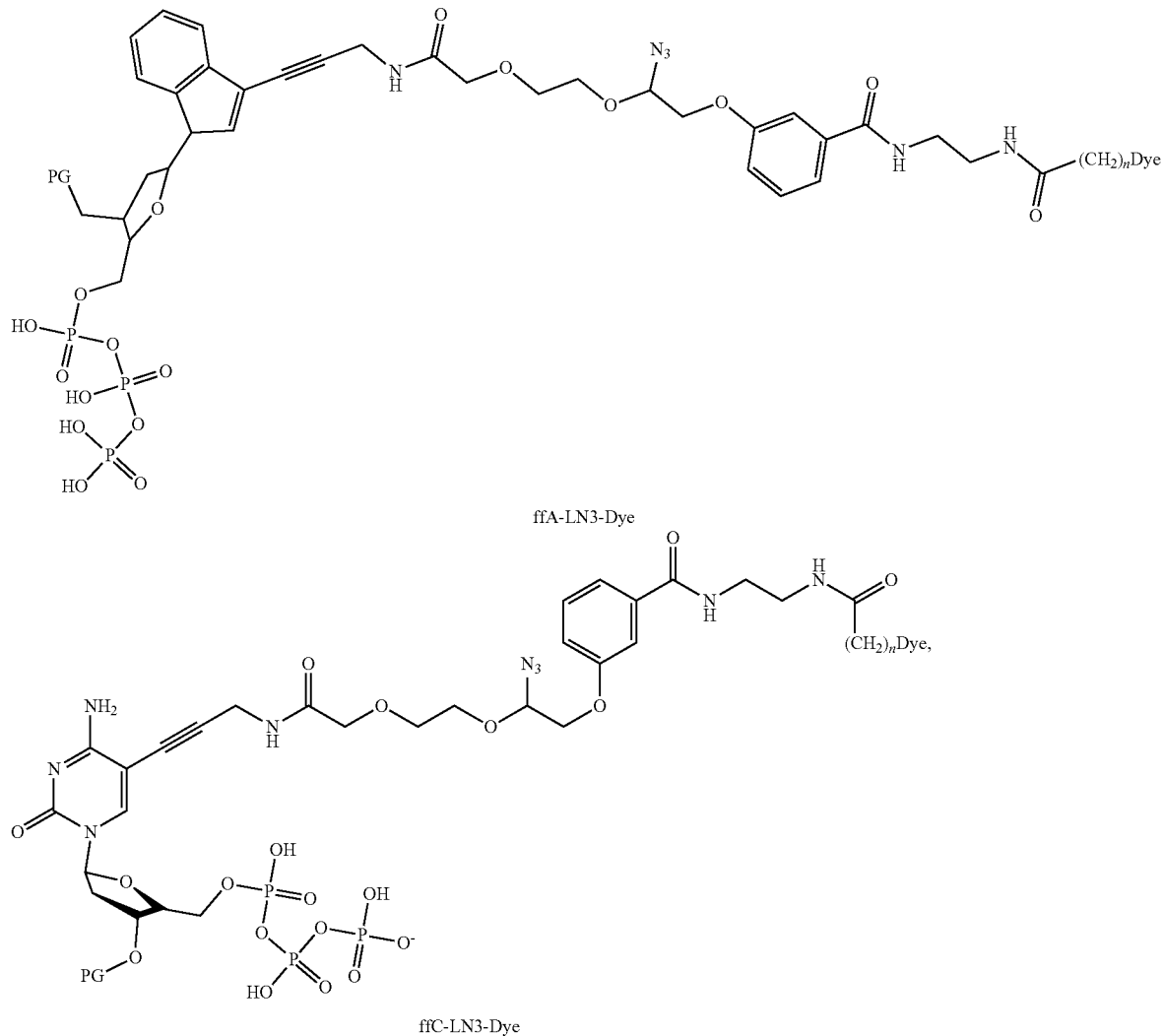

ffA-LN3-Dye ffC-LN3-Dye where PG stands for the 3' hydroxy blocking groups described herein.

Kits

The present disclosure also provides kits including labeled nucleotides described herein. Such kits will generally include at least one nucleotide labeled with a dye (for example, a photoswitchable dye described herein) together with at least one further component. The further component(s) may be one or more of the components identified in a method set forth herein or in the Examples section below. Some non-limiting examples of components that can be combined into a kit of the present disclosure are set forth below.

In a particular embodiment, a kit can include at least one labeled nucleotide or nucleoside together with labeled or unlabeled nucleotides or nucleosides. For example, nucleotides labeled with dyes may be supplied in combination with unlabeled or native nucleotides, and/or with fluorescently labeled nucleotides or any combination thereof. Combinations of nucleotides may be provided as separate individual components (e.g., one nucleotide type per vessel or tube) or as nucleotide mixtures (e.g., two or more nucleotides mixed in the same vessel or tube). In some embodiments, one or more dyes are selected from the photoswitchable dyes disclosed herein.

Where kits comprise a plurality, particularly two, or three, or more particularly four, labeled nucleotides each labeled with a dye compound, the different nucleotides may be labeled with different dye compounds, or one may be dark, with no dye compounds. Where the different nucleotides are labeled with different dye compounds, it is a feature of the kits that the dye compounds are spectrally distinguishable fluorescent dyes through one or more imaging events. When two nucleotides labeled with fluorescent dye compounds are supplied in kit form, it is a feature of some embodiments that the spectrally distinguishable fluorescent dyes can be excited at the same wavelength, such as, for example by the same laser. When four nucleotides labeled with fluorescent dye compounds are supplied in kit form, it is a feature of some embodiments that two of the spectrally distinguishable fluorescent dyes can both be excited at one wavelength and the other two spectrally distinguishable dyes are not excited at such wavelength. In some embodiments, one of the four different type of nucleotides is not labeled.

Although kits are exemplified herein in regard to configurations having different nucleotides that are labeled with different dye compounds, it will be understood that kits can include 2, 3, 4 or more different nucleotides that have the same dye compound.

In particular embodiments, a kit may include a polymerase enzyme capable of catalyzing incorporation of the nucleotides into a polynucleotide. Other components to be included in such kits may include buffers and the like. The nucleotides of the present disclosure, and other any nucleotide components including mixtures of different nucleotides, may be provided in the kit in a concentrated form to be diluted prior to use. In such embodiments a suitable dilution buffer may also be included. Again, one or more of the components identified in a method set forth herein can be included in a kit of the present disclosure.

Some embodiments of the present disclosure relate to a kit comprising at least one type of labeled nucleotide, wherein the nucleotide is labeled with a photoswitchable dye described herein. In some further embodiment, the kit comprises two or more types of different nucleotides, wherein a first type of nucleotides is labeled with a first photoswitchable label described herein and the second type of nucleotides is labeled with the second photoswitchable label described herein. In further embodiments, the kit may comprises a third type of nucleotide comprises a label that emits at the same or substantially same wavelength as the first photoswitchable label, or comprises a label that may be excited using the same or substantially same excitation wavelength as the first photoswitchable label. In further embodiments, the kit may comprise a fourth type of nucleotide that is unlabeled. In some embodiments, the first type, the second type, and the third type of nucleotides may be measured by detection at the same wavelength.

In any embodiments of the kit described herein, it may be used on an automated sequencing instrument, wherein the automated sequencing instrument comprises two lasers operating at different excitation wavelengths, and a detection system having a single detection channel set to a fixed emission wavelength.

In addition to the fluorescent moieties disclosed in the photoswitchable labels, other exemplary fluorescent moieties, or derivatives thereof, for use as fluorescent moieties include, but are not limited to, fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzoindolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malacite green, stilbene, DEG dyes (for example as those described in US2010/0009353, incorporated herein by reference in its entirety), NR dyes, near-infrared dyes and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), Hermanson, Bioconjugate Techniques, 2nd Edition, US2010/0009353 or WO 98/59066, each of which is incorporated by reference in their entireties. In some embodiments, the third label described herein may also be selected from any of the exemplary fluorescent moieties, or derivatives thereof as noted herein.

Sequencing Applications

Labeled nucleotides or nucleosides according to the present disclosure may be used in any method of analysis such as method that include detection of a fluorescent label attached to a nucleotide or nucleoside, whether on its own or incorporated into or associated with a larger molecular structure or conjugate. In this context the term "incorporated into a polynucleotide" can mean that the 5' phosphate is joined in phosphodiester linkage to the 3' hydroxy group of a second (modified or unmodified) nucleotide, which may itself form part of a longer polynucleotide chain. The 3' end of a nucleotide set forth herein may or may not be joined in phosphodiester linkage to the 5' phosphate of a further (modified or unmodified) nucleotide. Thus, in one non-limiting embodiment, the disclosure provides a method of detecting a nucleotide incorporated into a polynucleotide which comprises: (a) incorporating at least one nucleotide of the disclosure into a polynucleotide and (b) detecting the nucleotide(s) incorporated into the polynucleotide by detecting the fluorescent signal from the dye compound attached to the nucleotide(s).

This method can include: a synthetic step (a) in which one or more nucleotides according to the disclosure are incorporated into a polynucleotide and a detection step (b) in which one or more nucleotide(s) incorporated into the polynucleotide are detected by detecting or quantitatively measuring their fluorescence.

Some embodiments of the present application are directed to methods of sequencing including: (a) incorporating at least one labeled nucleotide as described herein into a polynucleotide; and (b) detecting the labeled nucleotide(s) incorporated into the polynucleotide by detecting the fluorescent signal from the new fluorescent dye attached to the nucleotide(s).

In one embodiment, at least one nucleotide is incorporated into a polynucleotide in the synthetic step by the action of a polymerase enzyme. However, other methods of joining nucleotides to polynucleotides, such as, for example, chemical oligonucleotide synthesis or ligation of labeled oligonucleotides to unlabeled oligonucleotides, can be used. Therefore, the term "incorporating," when used in reference to a nucleotide and polynucleotide, can encompass polynucleotide synthesis by chemical methods as well as enzymatic methods.

In a specific embodiment, a synthetic step is carried out and may optionally comprise incubating a template polynucleotide strand with a reaction mixture comprising fluorescently labeled nucleotides of the disclosure. A polymerase can also be provided under conditions which permit formation of a phosphodiester linkage between a free 3' hydroxy group on a polynucleotide strand annealed to the template polynucleotide strand and a 5' phosphate group on the nucleotide. Thus, a synthetic step can include formation of a polynucleotide strand as directed by complementary base-pairing of nucleotides to a template strand.

In all embodiments of the methods, the detection step may be carried out while the polynucleotide strand into which the labeled nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the labeled nucleotide(s) may be isolated or purified and then processed further or used in a subsequent analysis. By way of example, target polynucleotides labeled with nucleotide(s) as described herein in a synthetic step may be subsequently used as labeled probes or primers. In other embodiments, the product of the synthetic step set forth herein may be subject to further reaction steps and, if desired, the product of these subsequent steps purified or isolated.

Suitable conditions for the synthetic step will be well known to those familiar with standard molecular biology techniques. In one embodiment, a synthetic step may be analogous to a standard primer extension reaction using nucleotide precursors, including nucleotides as described herein, to form an extended target strand complementary to the template strand in the presence of a suitable polymerase enzyme. In other embodiments, the synthetic step may itself form part of an amplification reaction producing a labeled double stranded amplification product comprised of annealed complementary strands derived from copying of the target and template polynucleotide strands. Other exemplary synthetic steps include nick translation, strand displacement polymerization, random primed DNA labeling, etc. A particularly useful polymerase enzyme for a synthetic step is one that is capable of catalyzing the incorporation of nucleotides as set forth herein. A variety of naturally occurring or modified polymerases can be used. By way of example, a thermostable polymerase can be used for a synthetic reaction that is carried out using thermocycling conditions, whereas a thermostable polymerase may not be desired for isothermal primer extension reactions. Suitable thermostable polymerases which are capable of incorporating the nucleotides according to the disclosure include those described in WO 2005/024010 or WO06120433, each of which is incorporated herein by reference. In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments, the disclosure encompasses methods of nucleic acid sequencing, re-sequencing, whole genome sequencing, single nucleotide polymorphism scoring, any other application involving the detection of the labeled nucleotide or nucleoside set forth herein when incorporated into a polynucleotide. Any of a variety of other applications benefitting the use of polynucleotides labeled with the nucleotides comprising fluorescent dyes can use labeled nucleotides or nucleosides with dyes set forth herein.

In a particular embodiment, the disclosure provides use of labeled nucleotides according to the disclosure in a polynucleotide sequencing-by-synthesis reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) can be determined in a detection or "imaging" step. The identity of the added base may be determined after each nucleotide incorporation step. The sequence of the template may then be inferred using conventional Watson-Crick base-pairing rules. The use of the labeled nucleotides set forth herein for determination of the identity of a single base may be useful, for example, in the scoring of single nucleotide polymorphisms, and such single base extension reactions are within the scope of this disclosure.

In an embodiment of the present disclosure, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide can be primed with a suitable primer (or prepared as a hairpin construct which will contain the primer as part of the hairpin), and the nascent chain is extended in a stepwise manner by addition of nucleotides to the 3' end of the primer in a polymerase-catalyzed reaction.

In particular embodiments, each of the different nucleotide triphosphates (A, T, G and C) may be labeled with a unique fluorophore and also comprises a blocking group at the 3' position to prevent uncontrolled polymerization. Alternatively, one of the four nucleotides may be unlabeled (dark). The polymerase enzyme incorporates a nucleotide into the nascent chain complementary to the template polynucleotide, and the blocking group prevents further incorporation of nucleotides. Any unincorporated nucleotides can be washed away and the fluorescent signal from each incorporated nucleotide can be "read" optically by suitable means, such as a charge-coupled device using laser excitation and suitable emission filters. The 3'-blocking group and fluorescent dye compounds can then be removed (deprotected) simultaneously or sequentially to expose the nascent chain for further nucleotide incorporation. Typically, the identity of the incorporated nucleotide will be determined after each incorporation step, but this is not strictly essential. Similarly, U.S. Pat. No. 5,302,509 (which is incorporated herein by reference) discloses a method to sequence polynucleotides immobilized on a solid support.

The method, as exemplified above, utilizes the incorporation of fluorescently labeled, 3'-blocked nucleotides A, G, C, and T into a growing strand complementary to the immobilized polynucleotide, in the presence of DNA polymerase. The polymerase incorporates a base complementary to the target polynucleotide but is prevented from further addition by the 3'-blocking group. The label of the incorporated nucleotide can then be determined, and the blocking group removed by chemical cleavage to allow further polymerization to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxy group that serves as a primer or initiation point for the addition of further nucleotides in the sequencing reaction. The region of the template to be sequenced will overhang this free 3' hydroxy group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments, sequencing may proceed by strand displacement. In certain embodiments, a primer bearing the free 3' hydroxy group may be added as a separate component (e.g., a short oligonucleotide) that hybridizes to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in PCT Publication Nos. WO 01/57248 and WO 2005/047301, each of which is incorporated herein by reference. Nucleotides can be added successively to a growing primer, resulting in synthesis of a polynucleotide chain in the 5' to 3' direction. The nature of the base which has been added may be determined, particularly but not necessarily after each nucleotide addition, thus providing sequence information for the nucleic acid template. Thus, a nucleotide is incorporated into a nucleic acid strand (or polynucleotide) by joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments, the nucleic acid template to be sequenced may be attached to a solid support via any suitable linkage method known in the art, for example via covalent attachment. In certain embodiments template polynucleotides may be attached directly to a solid support (e.g., a silica-based support). However, in other embodiments of the disclosure the surface of the solid support may be modified in some way so as to allow either direct covalent attachment of template polynucleotides, or to immobilize the template polynucleotides through a hydrogel or polyelectrolyte multilayer, which may itself be non-covalently attached to the solid support.

Arrays in which polynucleotides have been directly attached to silica-based supports are those for example disclosed in WO 00/06770 (incorporated herein by reference), wherein polynucleotides are immobilized on a glass support by reaction between a pendant epoxide group on the glass with an internal amino group on the polynucleotide. In addition, polynucleotides can be attached to a solid support by reaction of a sulfur-based nucleophile with the solid support, for example, as described in WO 2005/047301 (incorporated herein by reference). A still further example of solid-supported template polynucleotides is where the template polynucleotides are attached to hydrogel supported upon silica-based or other solid supports, for example, as described in WO 00/31148, WO 01/01143, WO 02/12566, WO 03/014392, U.S. Pat. No. 6,465,178 and WO 00/53812, each of which is incorporated herein by reference.

A particular surface to which template polynucleotides may be immobilized is a polyacrylamide hydrogel. Polyacrylamide hydrogels are described in the references cited above and in WO2005/065814, which is incorporated herein by reference. Specific hydrogels that may be used include those described in WO 2005/065814 and U.S. Pub. No. 2014/0079923. In one embodiment, the hydrogel is PAZAM (poly(N-(5-azidoacetamidylpentyl) acrylamide-co-acrylamide)).

DNA template molecules can be attached to beads or microparticles, for example, as described in U.S. Pat. No. 6,172,218 (which is incorporated herein by reference). Attachment to beads or microparticles can be useful for sequencing applications. Bead libraries can be prepared where each bead contains different DNA sequences. Exemplary libraries and methods for their creation are described in *Nature*, 437, 376-380 (2005); *Science*, 309, 5741, 1728-1732 (2005), each of which is incorporated herein by reference. Sequencing of arrays of such beads using nucleotides set forth herein is within the scope of the disclosure.

Template(s) that are to be sequenced may form part of an "array" on a solid support, in which case the array may take any convenient form. Thus, the method of the disclosure is applicable to all types of high-density arrays, including single-molecule arrays, clustered arrays, and bead arrays. Labeled nucleotides of the present disclosure may be used for sequencing templates on essentially any type of array, including but not limited to those formed by immobilization of nucleic acid molecules on a solid support.

However, labeled nucleotides of the disclosure are particularly advantageous in the context of sequencing of clustered arrays. In clustered arrays, distinct regions on the array (often referred to as sites, or features) comprise multiple polynucleotide template molecules. Generally, the multiple polynucleotide molecules are not individually resolvable by optical means and are instead detected as an ensemble. Depending on how the array is formed, each site on the array may comprise multiple copies of one individual polynucleotide molecule (e.g., the site is homogenous for a particular single- or double-stranded nucleic acid species) or even multiple copies of a small number of different polynucleotide molecules (e.g., multiple copies of two different nucleic acid species). Clustered arrays of nucleic acid molecules may be produced using techniques generally known in the art. By way of example, WO 98/44151 and WO 00/18957, each of which is incorporated herein, describe methods of amplification of nucleic acids wherein both the template and amplification products remain immobilized on a solid support in order to form arrays comprised of clusters or "colonies" of immobilized nucleic acid molecules. The nucleic acid molecules present on the clustered arrays prepared according to these methods are suitable templates for sequencing using the nucleotides labeled with dye compounds of the disclosure.

The labeled nucleotides of the present disclosure are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to individually resolve the individual polynucleotide molecules. The target nucleic acid molecules immobilized onto the surface of the solid support can thus be capable of being resolved by optical means in some embodiments. This means that one or more distinct signals, each representing one polynucleotide, will occur within the resolvable area of the particular imaging device used.

Single molecule detection may be achieved wherein the spacing between adjacent polynucleotide molecules on an array is at least 100 nm, more particularly at least 250 nm, still more particularly at least 300 nm, even more particularly at least 350 nm. Thus, each molecule is individually resolvable and detectable as a single molecule fluorescent point, and fluorescence from the single molecule fluorescent point also exhibits single step photobleaching.

The terms "individually resolved" and "individual resolution" are used herein to specify that, when visualized, it is possible to distinguish one molecule on the array from its neighboring molecules. Separation between individual molecules on the array will be determined, in part, by the particular technique used to resolve the individual molecules. The general features of single molecule arrays will be understood by reference to published applications WO 00/06770 and WO 01/57248, each of which is incorporated herein by reference. Although one use of the nucleotides of the disclosure is in sequencing-by-synthesis reactions, the utility of the nucleotides is not limited to such methods. In fact, the nucleotides may be used advantageously in any sequencing methodology which requires detection of fluorescent labels attached to nucleotides incorporated into a polynucleotide.

In particular, the labeled nucleotides of the disclosure may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labeled dideoxynucleotides in a primer extension sequencing reaction. So-called Sanger sequencing methods, and related protocols (Sanger-type), utilize randomized chain termination with labeled dideoxynucleotides.

Thus, the present disclosure also encompasses labeled nucleotides which are dideoxynucleotides lacking hydroxyl groups at both of the 3' and 2' positions, such dideoxynucleotides being suitable for use in Sanger type sequencing methods and the like.

Labeled nucleotides of the present disclosure incorporating 3' blocking groups, it will be recognized, may also be of utility in Sanger methods and related protocols since the same effect achieved by using dideoxy nucleotides may be achieved by using nucleotides having 3'-OH blocking groups: both prevent incorporation of subsequent nucleotides. Where nucleotides according to the present disclosure, and having a 3' blocking group are to be used in Sanger-type sequencing methods it will be appreciated that the dye compounds or detectable labels attached to the nucleotides need not be connected via cleavable linkers, since in each instance where a labeled nucleotide of the disclosure is incorporated; no nucleotides need to be subsequently incorporated and thus the label need not be removed from the nucleotide.

An additional embodiment as disclosed herein provides a method for determining a plurality of nucleic acid sequences comprising providing a sample comprising plurality of different nucleic acids, each nucleic acid comprising a template and primer; performing a cycle of a sequencing reaction, wherein the cycle comprises extending the primers for the nucleic acids in the sample to form a plurality of extended primers having at least four different labeled nucleotide types as described herein, thereby forming an extended sample, acquiring a first collection of signals from the extended sample, wherein at least two of the different nucleotide types in the extended primers are in a signal state and at least one the different nucleotide types in the extended primers is in a dark state; irradiating the polynucleotides with a light source to cause changes in emission signals certain nucleotide label(s), and acquiring a second collection of signals from the sample, wherein two the different nucleotide types are in different state in the first collection of signals compared to the second collection of signals; and determining sequences for the plurality of different nucleic acids by evaluating the first collection of signals and the second collection of signals from the cycles. In some embodiments, the plurality of different nucleic acids is attached to a substrate. In some embodiments, the extending of the primers comprises polymerase catalyzed addition of the different nucleotide types. In some embodiments, the different nucleotide types comprise reversible blocking moieties, whereby a single nucleotide type is added to each of the extended primers in each of the cycles. In some embodiments, the extending of the primers comprises ligase catalyzed addition of oligonucleotides comprising the different nucleotide types. In some embodiments, two of the different nucleotide types in the extended primers are in a dark state during the acquiring of the first collection of signals from the extended sample. In preferred embodiments, a sequencing reaction cycle as previously described is repeated one or more times.

EXAMPLES

Additional embodiments are disclosed in further detail in the following examples, which are not in any way intended to limit the scope of the claims.

Example 1

Figure 2:
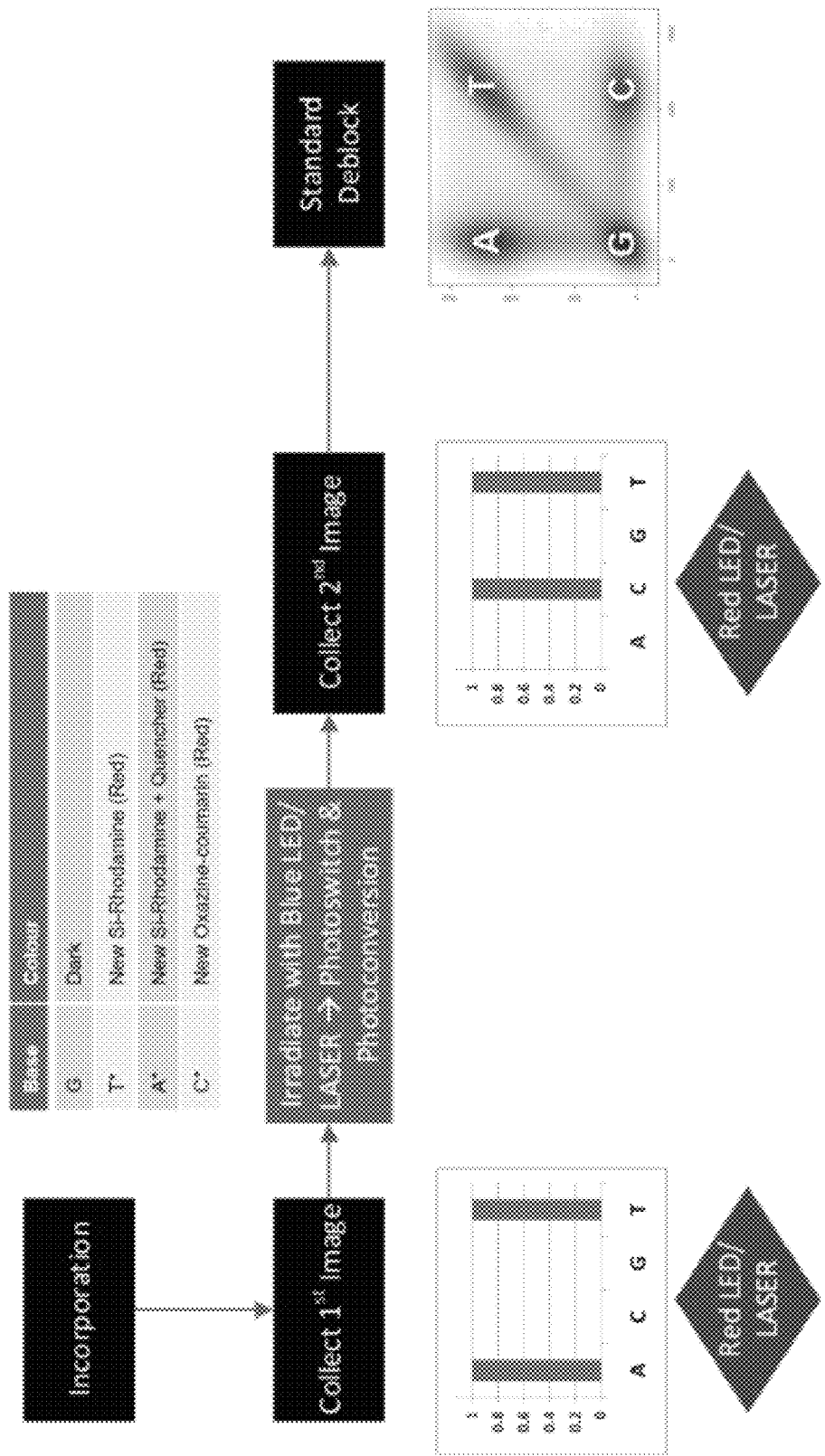
FIG. 2 illustrates a flow chart for a one-channel sequencing process using the photoswitchable dyes disclosed herein.

In this example, a simplified approach to obtain incorporated dye discrimination based on modified photoswitchable red-emitting fluorophores is described and the workflow of one cycle of incorporation is illustrated in FIG. 2.

The structure and function of each base-tethered fluorescent tag required for this approach is shown in Table 1. The "A" and "C" dyes have the capability to be photoswitched. The "T" dye may be a standard red emitting dye, for example, may be the same red dye that is part of the photoswitchable dyad for "A" nucleotide. The linker that connects the dye to the nucleotide is the LN3 linker described herein, only partially shown in Table 1 and the photochemical reaction schemes below. Other linkers disclosed herein may also be used. All of these dyes are able to function in biologically-relevant media.

TABLE 1
| Base | Fluorescent Label Structure | Function |
|---|---|---|
| G | n/a (unlabeled) | Std incorporation |
| T | 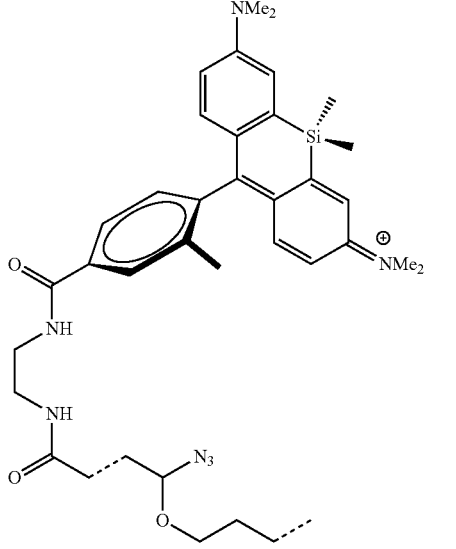 | Std incorporation |
| A | 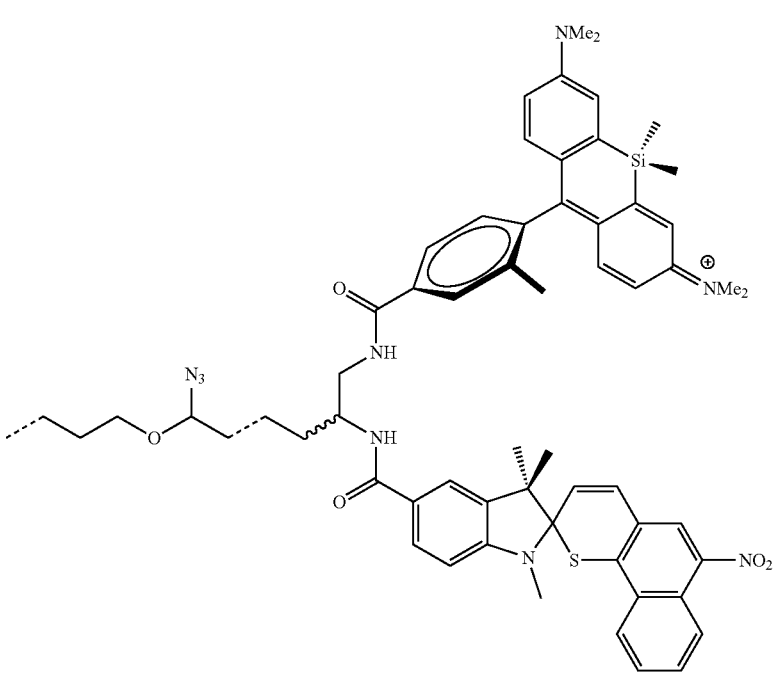 | Std incorporation; switched to a quenched "off" state after blue LED irradiation. |

TABLE 1-continued

| Base | Fluorescent Label Structure | Function |
|------|------------------------------|----------|
| C | | Std incorporation; switched to an "on" state after blue LED irradiation. |

The new A dye is designed such that it can be photo-switched using a blue laser or LED (at 405 nm). Photochemical activation leads to a ring-opening reaction that converts the bottom portion of the dyad into a quencher capable of suppressing the emission from the Si-containing rhodamine dye (Scheme 1).

Scheme 1. Photochemical quenching of dyad with silicon-containing rhodamine fluorescent moiety.

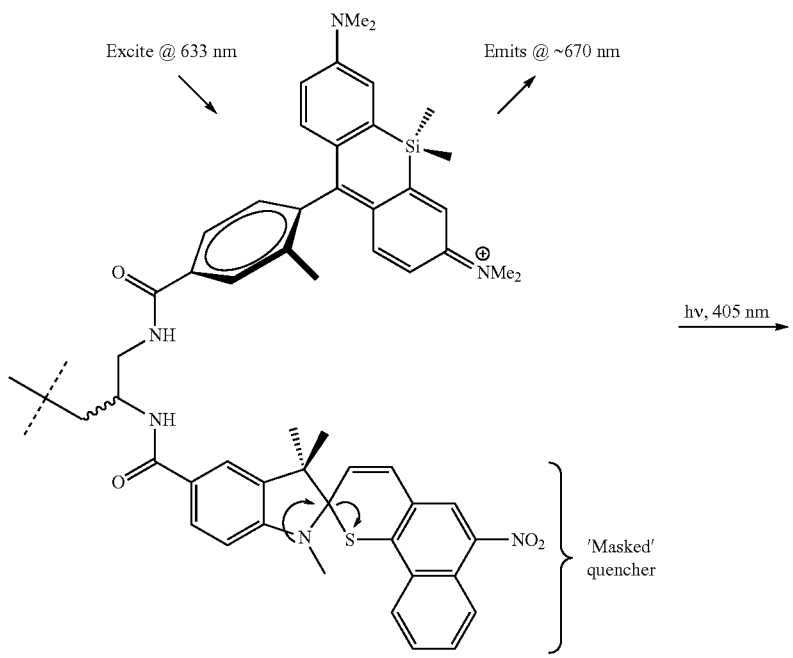

-continued

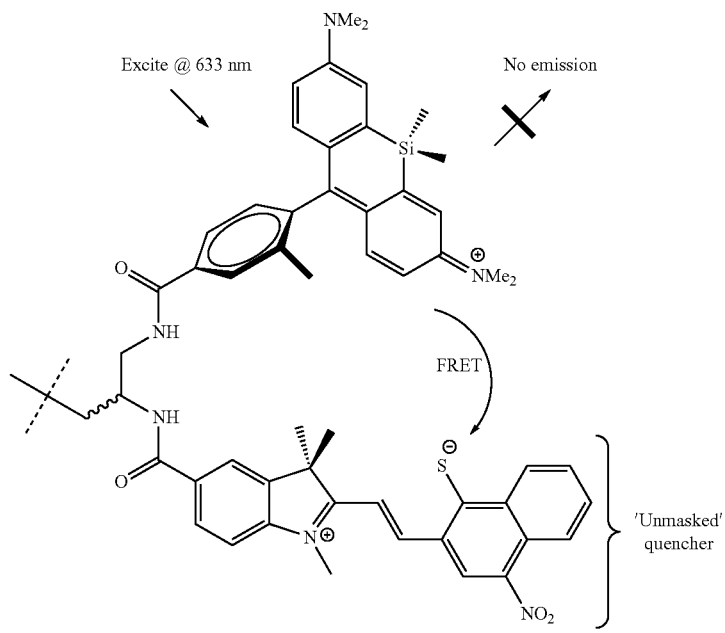

The photoactivatable C dye can be switched to an "on" fluorescent state by exposure to blue laser or LED irradiation (at 405 nm) during the same time as the A dye would be converted into a quenched "off" state. For the C dye, a similar ring-opening reaction opens the oxazine ring reversibly generating a highly fluorescent state with a maximum absorbance centered at around 550-650 nm (Scheme 2). Therefore, all the dyes suggested here could be excited with the same red LED or laser (at 633 nm).

Scheme 2. Photochemical activation of dyad with silicon-containing rhodamine fluorescent moiety.

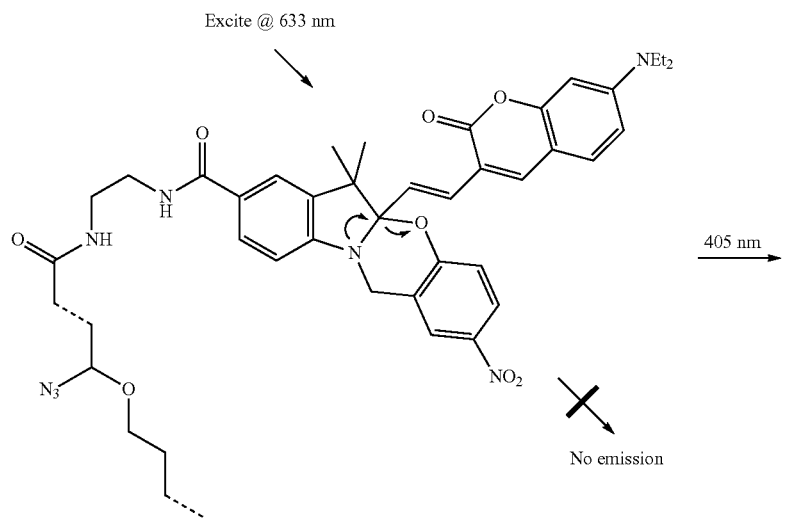

-continued

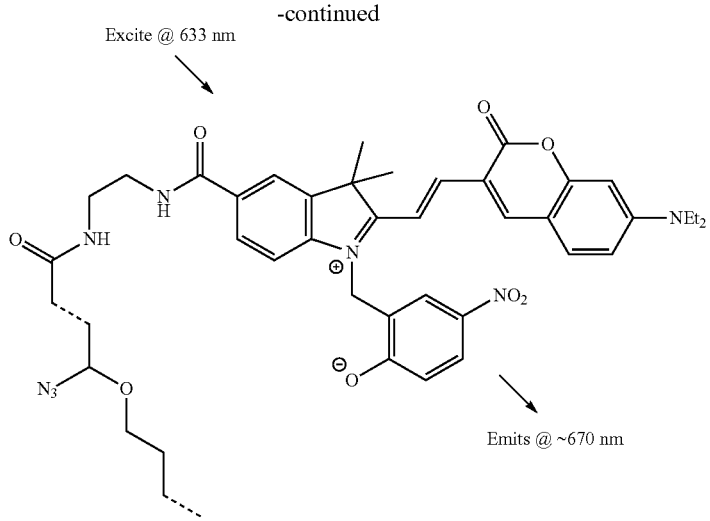

In FIG. 2, four different kind of nucleotides according to Table 1 are exposed to a flowcell for incorporation into polynucleotides. During the first imaging step, the light emission from each cluster is recorded. In this first imaging event, the fluorescent signals emitted from both "A" and "T" nucleotides are detected. Then, a blue laser with 405 nm wavelength is used to quench the "A" dye and activate the "C" dye. Then a second imaging step is taken place and the light emission from each cluster is recorded again. In this second imaging event, the fluorescent signals emitted from the "C" and "T" nucleotides are detected. At both imaging events, "G" nucleotide is dark (unlabeled). Nucleotides are identified by analysis of the different emission patterns for each base across the two images. The combination of Image 1 and Image 2 are processed by image analysis software to identify which bases are incorporated at each cluster position. After the second imaging event, the incorporated nucleotides are deblocked following standard procedure to allow for the incorporation of another nucleotide. This sequencing cycle is repeated "n" times to create a read length of "n" bases.

In this example, a blue laser or LED at 405 nm is used, which may further be adjusted by introducing additional substituents at the coumarin portion of the "C" dye or the spironaphthothiopyran portion of the "A" dye. This would allow complete compatibility with the current iSeq™ system with a 450 nm laser. The proposed modification would also reduce the likelihood of possible DNA damage that may result from repeated exposure to higher energy irradiation over several sequencing cycles.

What is claimed is:

1. A kit comprising four types of nucleotides for sequencing by synthesis, wherein a first type of nucleotide is a labeled nucleotide conjugate comprising a first photoswitchable label, wherein the first photoswitchable label comprises a silicon rhodamine fluorescent moiety covalently bonded, optionally via a first linker, to a first photochromic moiety, a second type of nucleotide is a labeled nucleotide conjugate comprising a second photoswitchable label, wherein the second photoswitchable label comprises a coumarin fluorescent moiety covalently bonded, optionally via a second linker, to a second photochromic moiety, a third type of nucleotide comprises a label having an emission at substantially the same wavelength region as the first type of nucleotide or the second type of nucleotide, and a fourth type of nucleotide is unlabeled.

2. The kit of claim 1, wherein the first type of nucleotide, the second type of nucleotide, and the third type of nucleotide are detectable at the same detection channel.

3. The kit according to claim 1, for use on an automated sequencing instrument, wherein the automated sequencing instrument comprises a detection system having a single detection channel set to a fixed emission wavelength.

4. The kit of claim 1, wherein the first photochromic moiety comprises a spiropyrano or spirothiopyrano moiety.

5. The kit of claim 4, wherein the first photochromic moiety comprises a structure of formula (I):

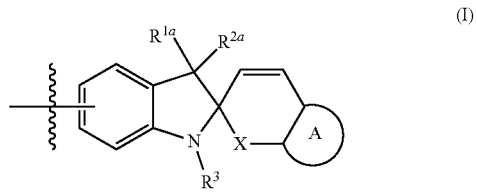

wherein:
X is O (oxygen) or S (sulfur);
each of $R^{1a}$ and $R^{2a}$ is independently selected from the group consisting of H, halo, optionally substituted $C_{1-6}$ alkyl, optionally substituted $C_{2-6}$ alkenyl, optionally substituted $C_{2-6}$ alkynyl, $C_{1-6}$ haloalkyl, $C_{1-6}$ alkoxy, and $C_{1-6}$ haloalkoxy;
$R^3$ is selected from the group consisting of H, $C_{1-6}$ alkyl, and $-(CH_2)_n-R^4$, $R^4$ is selected from the group consisting of $C_{6-10}$ aryl, 5 to 10 membered heteroaryl, 3 to 7 membered carbocyclyl, and 3 to 7 membered heterocyclyl, each optionally substituted;
ring A is $C_{6-10}$ aryl or 5 to 10 membered heteroaryl, each substituted with at least one electron withdrawing group; and
n is an integer of 1 to 6.

6. The kit of claim 5, wherein X is S.

7. The kit of claim 5, wherein each $R^{1a}$ and $R^{2a}$ is $C_{1-6}$ alkyl.

8. The kit of claim 5, wherein ring A is phenyl or naphthyl substituted with at least one electron withdrawing group selected from the group consisting of nitro, cyano, fluoro, bromo, —S(O₂)OH, —S(O)₂CF₃, ammonium, alkyl ammonium, and C₁₋₆ alkyl substituted with one or more fluoro or bromo.

9. The kit of claim 4, wherein the first photochromic moiety comprises the structure of formula (Ia):

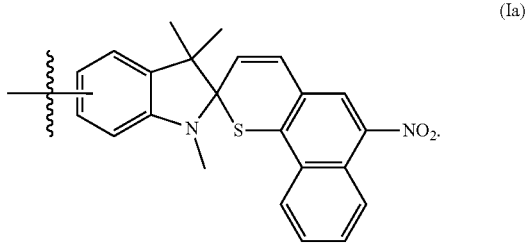

(Ia)

10. The kit of claim 1, wherein the first photoswitchable label comprises the structure:

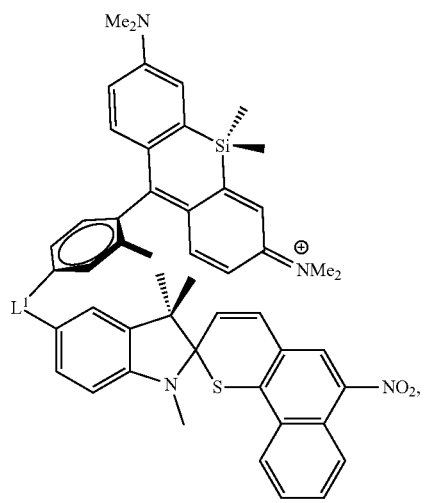

wherein L¹ is the first linker.

11. The kit of claim 1, wherein the second photochromic moiety comprises an oxazine moiety or a thiazine moiety.

12. The kit of claim 11, wherein the second photochromic moiety comprises a structure of formula (II):

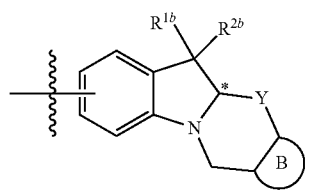

(II)

wherein:
Y is O (oxygen) or S (sulfur);
each of $R^{1b}$ and $R^{2b}$ is independently selected from the group consisting of H, halo, optionally substituted C₁₋₆ alkyl, optionally substituted C₂₋₆ alkenyl, optionally substituted C₂₋₆ alkynyl, C₁₋₆ haloalkyl, C₁₋₆ alkoxy, and C₁₋₆ haloalkoxy; and
ring B is C₆₋₁₀ aryl or 5 to 10 membered heteroaryl; each substituted with at least one electron withdrawing group; and
wherein * indicates the attachment point to the coumarin fluorescent moiety.

13. The kit of claim 12, wherein Y is O.

14. The kit of claim 12, wherein each $R^{1b}$ and $R^{2b}$ is C₁₋₆ alkyl.

15. The kit of claim 12, wherein ring B is phenyl or naphthyl substituted with at least one electron withdrawing group selected from the group consisting of nitro, cyano, fluoro, bromo, —S(O₂)OH, —S(O)₂CF₃, ammonium, alkyl ammonium, and C₁₋₆ alkyl substituted with one or more fluoro or bromo.

16. The kit of claim 11, wherein the second photochromic moiety comprises the structure of formula (IIa):

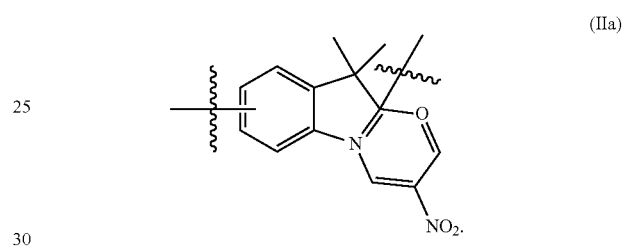

(IIa)

17. The kit of claim 1, wherein the second photoswitchable label comprises the structure:

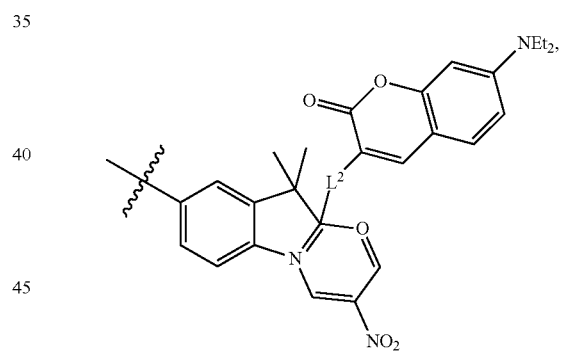

wherein L² is the second linker.

18. The kit of claim 1, wherein each of the first and the second photoswitchable label is attached to the nucleobase of the nucleotide conjugate through a cleavable linker.

19. The kit of claim 1, wherein the first photoswitchable label is excitable at an excitation wavelength in the range from about 550 nm to about 650 nm.

20. The kit of claim 19, wherein the first photoswitchable label is excitable at the excitation wavelength of about 633 nm.

21. The kit of claim 19, wherein the second photoswitchable label is excitable at substantially the same excitation wavelength as the first photoswitchable label.

* * * * *

UNITED STATES PATENT AND TRADEMARK OFFICE
CERTIFICATE OF CORRECTION

PATENT NO. : 11,959,138 B2
APPLICATION NO. : 17/867018
DATED : April 16, 2024
INVENTOR(S) : Wayne N. George et al.

It is certified that error appears in the above-identified patent and that said Letters Patent is hereby corrected as shown below:

In the Specification

Column 6, Line 8, delete "differentiatable" and insert -- differentiable --.

Column 7, Line 53, delete "$C_6\_o$" and insert -- $C_{6\text{-}10}$ --.

Column 10, Line 63, delete "phnoxynaphthacene" and insert -- phenoxynaphthacene --.

Column 17, Line 18, delete "isoquinlinyl," and insert -- isoquinolinyl, --.

Column 17, Line 24, delete "isoxazollylalkyl," and insert -- isoxazolylalkyl, --.

Column 29, Line 5, delete "–$CH_2N3$)" and insert -- –$CH_2N_3$) --.

Column 34, Line 12 (approx.), delete "Malacite" and insert -- Malachite --.

In the Claims

Column 50, Line 19, Claim 16, delete "formula (Ha):" and insert -- formula (IIa): --.

Signed and Sealed this
Twenty-fourth Day of September, 2024

Katherine Kelly Vidal
*Director of the United States Patent and Trademark Office*